US011781993B2

(12) United States Patent
Leo et al.

(10) Patent No.: US 11,781,993 B2
(45) Date of Patent: Oct. 10, 2023

(54) METHODS AND SENSORS FOR DETECTION

(71) Applicant: University of Florida Research Foundation, Inc., Gainesville, FL (US)

(72) Inventors: Sin Yen Leo, Gainesville, FL (US); Peng Jiang, Gainesville, FL (US); Tianwei Xie, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 17/903,312

(22) Filed: Sep. 6, 2022

(65) Prior Publication Data

US 2023/0025651 A1    Jan. 26, 2023

Related U.S. Application Data

(63) Continuation of application No. 16/611,745, filed as application No. PCT/US2018/033173 on May 17, 2018, now Pat. No. 11,467,094.
(Continued)

(51) Int. Cl.
*G01N 21/78* (2006.01)
*G01N 21/25* (2006.01)
(Continued)

(52) U.S. Cl.
CPC ......... *G01N 21/78* (2013.01); *C08G 18/6755* (2013.01); *C08G 18/81* (2013.01);
(Continued)

(58) Field of Classification Search
CPC ...... G01N 21/78; G01N 21/25; G01N 21/255; G01N 21/272; G01N 33/2852;
(Continued)

(56) References Cited

U.S. PATENT DOCUMENTS 3,422,535 A    1/1969   Johnson
3,671,105 A    6/1972   Williams et al.
(Continued)

FOREIGN PATENT DOCUMENTS

CN    103935057 A    7/2014
CN    105036068 A    11/2015
(Continued)

OTHER PUBLICATIONS

Wang et al., "Photonic Crystal Structures with Tunable Structure Color as Colorimetric Sensors", 2013, Sensors, 13(4), 4192-4213 (Year: 2013).*
(Continued)

*Primary Examiner* — Samuel P Siefke
*Assistant Examiner* — Henry H Nguyen
(74) *Attorney, Agent, or Firm* — THOMAS|HORSTEMEYER, LLP

(57) ABSTRACT

Embodiments of the present disclosure provide for methods of detecting, sensors (e.g., chromogenic sensor), kits, compositions, and the like that related to or use tunable macroporous polymer. In an aspect, tunable macroporous materials as described herein can be used to determine the presence of a certain type(s) and quantity of liquid in a liquid mixture.

5 Claims, 11 Drawing Sheets

Related U.S. Application Data

(60) Provisional application No. 62/507,294, filed on May 17, 2017.

(51) Int. Cl.

| | | |
|---|---|---|
| *G01N 21/27* | (2006.01) | |
| *G01N 33/28* | (2006.01) | |
| *G01N 21/77* | (2006.01) | |
| *G02B 1/00* | (2006.01) | |
| *C08G 18/67* | (2006.01) | |
| *C08G 18/81* | (2006.01) | |
| *C08J 9/26* | (2006.01) | |
| *C08G 101/00* | (2006.01) | |

(52) U.S. Cl.
CPC ............... *C08J 9/26* (2013.01); *G01N 21/25* (2013.01); *G01N 21/255* (2013.01); *G01N 21/272* (2013.01); *G01N 33/2852* (2013.01); *C08G 2101/00* (2013.01); *C08G 2280/00* (2013.01); *C08J 2201/0442* (2013.01); *C08J 2205/044* (2013.01); *C08J 2375/14* (2013.01); *G01N 2021/7723* (2013.01); *G01N 2021/7773* (2013.01); *G02B 1/005* (2013.01)

(58) Field of Classification Search
CPC ... G01N 2021/7723; G01N 2021/7773; C08G 18/6755; C08G 18/81; C08G 2101/00; C08G 2280/00; C08J 9/26; C08J 2201/0442; C08J 2205/044; C08J 2375/14; G02B 1/005
See application file for complete search history.

(56) References Cited

U.S. PATENT DOCUMENTS

| | | | |
|---|---|---|---|
| 4,125,319 A | 11/1978 | Frank et al. | |
| 4,340,479 A | 7/1982 | Pall | |
| 4,664,748 A | 5/1987 | Ueno et al. | |
| 4,781,441 A | 11/1988 | Kanbe et al. | |
| 4,810,633 A | 3/1989 | Bauer et al. | |
| 5,147,716 A | 9/1992 | Bellus | |
| 5,337,018 A | 8/1994 | Yamagishi | |
| 5,429,743 A | 7/1995 | Geus et al. | |
| 5,529,524 A | 6/1996 | Jones | |
| 5,641,332 A | 6/1997 | Faber et al. | |
| 5,753,014 A | 5/1998 | Van Rijn | |
| 5,939,189 A | 8/1999 | Phillips et al. | |
| 5,948,470 A | 9/1999 | Harrison et al. | |
| 5,993,661 A | 11/1999 | Ruckenstein et al. | |
| 6,044,981 A | 4/2000 | Chu et al. | |
| 6,531,304 B1 | 3/2003 | Boennemann et al. | |
| 6,565,763 B1 | 5/2003 | Asakawa et al. | |
| 6,649,255 B1 | 11/2003 | Fain et al. | |
| 6,881,582 B2 | 4/2005 | Ratogi et al. | |
| 6,929,764 B2 | 8/2005 | Jiang et al. | |
| 6,958,137 B2 | 10/2005 | Lee et al. | |
| 7,351,470 B2 | 4/2008 | Draheim et al. | |
| 7,630,589 B2 | 12/2009 | Kilic et al. | |
| 7,691,325 B2 | 4/2010 | Chopra et al. | |
| 7,889,954 B2 | 2/2011 | Sailor et al. | |
| 9,233,883 B1 | 1/2016 | Rauscher et al. | |
| 9,272,947 B2 | 3/2016 | Baca et al. | |
| 10,189,967 B2 | 1/2019 | Jiang et al. | |
| 10,700,225 B2 | 6/2020 | Wang et al. | |
| 2003/0031438 A1 | 2/2003 | Kambe et al. | |
| 2004/0131779 A1 | 7/2004 | Haubrich et al. | |
| 2004/0131799 A1 | 7/2004 | Arsenault et al. | |
| 2005/0147807 A1 | 7/2005 | Haas et al. | |
| 2006/0137462 A1 | 6/2006 | Divigalpitiya et al. | |
| 2007/0036653 A1 | 2/2007 | Bak et al. | |
| 2007/0156079 A1 | 7/2007 | Brown | |
| 2007/0206270 A1 | 9/2007 | Iwamatsu et al. | |
| 2008/0006574 A1 | 1/2008 | Ramaswamy et al. | |
| 2008/0027199 A1 | 1/2008 | Mazurek et al. | |
| 2008/0185498 A1 | 8/2008 | Purdy et al. | |
| 2008/0233418 A1 | 9/2008 | Krueger | |
| 2008/0309923 A1 | 12/2008 | Falk | |
| 2009/0034051 A1 | 2/2009 | Arsenault et al. | |
| 2009/0274873 A1 | 11/2009 | Shinotsuka | |
| 2010/0051561 A1 | 3/2010 | Lee | |
| 2010/0058844 A1 | 3/2010 | Lin et al. | |
| 2010/0068168 A1 | 3/2010 | Song et al. | |
| 2010/0069726 A1 | 3/2010 | Levinson | |
| 2010/0125113 A1 | 5/2010 | Xiao et al. | |
| 2010/0150511 A1 | 6/2010 | Arsenault et al. | |
| 2010/0155325 A1 | 6/2010 | Zhang et al. | |
| 2010/0188732 A1 | 7/2010 | Akashi et al. | |
| 2010/0216310 A1 | 8/2010 | Metz et al. | |
| 2010/0218716 A1 | 9/2010 | Havens et al. | |
| 2010/0244169 A1 | 9/2010 | Maeda et al. | |
| 2010/0315703 A1 | 12/2010 | Purdy et al. | |
| 2011/0019277 A1 | 1/2011 | Sager et al. | |
| 2011/0097814 A1 | 4/2011 | Bommarito et al. | |
| 2011/0111173 A1 | 5/2011 | Ogawa et al. | |
| 2011/0140106 A1 | 6/2011 | Forbes | |
| 2011/0194261 A1 | 8/2011 | Tanaka et al. | |
| 2011/0212463 A1* | 9/2011 | Delouise | G01N 33/54386 435/7.1 |
| 2011/0233476 A1 | 9/2011 | Arsenault | |
| 2011/0255035 A1 | 10/2011 | Wu | |
| 2012/0051489 A1 | 3/2012 | Varanasi et al. | |
| 2012/0073388 A1 | 3/2012 | Chibante | |
| 2012/0074612 A1 | 3/2012 | Scrivens et al. | |
| 2012/0152338 A1 | 6/2012 | Ha et al. | |
| 2012/0225517 A1 | 9/2012 | Zhang et al. | |
| 2012/0262789 A1 | 10/2012 | Xie et al. | |
| 2012/0281292 A1 | 11/2012 | Baca et al. | |
| 2012/0293802 A1 | 11/2012 | Ozin et al. | |
| 2012/0309047 A1* | 12/2012 | Kotinas | G01N 21/78 436/95 |
| 2012/0313205 A1 | 12/2012 | Haddad et al. | |
| 2012/0321810 A1 | 12/2012 | Tebby et al. | |
| 2013/0078750 A1 | 3/2013 | Yeo et al. | |
| 2013/0215513 A1 | 8/2013 | Liang et al. | |
| 2013/0222881 A1 | 8/2013 | Aizenberg et al. | |
| 2013/0258483 A1 | 10/2013 | Pett et al. | |
| 2013/0320467 A1 | 12/2013 | Buchanan et al. | |
| 2013/0340824 A1 | 12/2013 | Oh et al. | |
| 2014/0017145 A1 | 1/2014 | Aizenberg et al. | |
| 2014/0092464 A1* | 4/2014 | Arsenault | G01N 21/7743 359/290 |
| 2014/0106468 A1 | 4/2014 | Boersma | |
| 2014/0166100 A1 | 6/2014 | Watanabe et al. | |
| 2014/0319524 A1 | 10/2014 | Phillips et al. | |
| 2015/0035269 A1 | 2/2015 | Hooper et al. | |
| 2015/0157453 A1 | 6/2015 | Nazirizadeh et al. | |
| 2015/0276989 A1 | 10/2015 | Han et al. | |
| 2016/0032141 A1 | 2/2016 | Maghsoodi et al. | |
| 2016/0254395 A1 | 9/2016 | Jiang et al. | |
| 2016/0326334 A1 | 11/2016 | Jiang et al. | |
| 2017/0038295 A1* | 2/2017 | Aizenberg | G02B 1/005 |
| 2017/0209045 A1 | 7/2017 | Choo et al. | |
| 2017/0215790 A1 | 8/2017 | Levinson et al. | |
| 2017/0225395 A1 | 8/2017 | Boydston et al. | |
| 2017/0271259 A1 | 9/2017 | Hotta et al. | |

FOREIGN PATENT DOCUMENTS

| | | | |
|---|---|---|---|
| EP | 0341675 | A2 | 11/1989 |
| EP | 2220520 | A2 | 8/2010 |
| WO | 9820388 | A1 | 5/1998 |
| WO | 1998020388 | A1 | 5/1998 |
| WO | 2000010934 | A1 | 3/2000 |
| WO | 02073699 | A3 | 11/2002 |
| WO | 2007070486 | A2 | 6/2007 |
| WO | 2008060322 | A2 | 5/2008 |
| WO | 2010007853 | A1 | 1/2010 |
| WO | 2015066337 | A1 | 5/2015 |
| WO | 2018213570 | A2 | 11/2018 |

(56) References Cited

OTHER PUBLICATIONS

International Search Report for International Application No. PCT/US2018/033173, dated Nov. 21, 2018.
Written Opinion for International Application No. PCT/US2018/033173, dated Nov. 21, 2018.
J.A. Hiller, J.D. Mendelsohn, M.F. Rubner, "Reversibly erasable nanoporous anti-reflection coatings from polyelectrolyte multilayers", Nat. Mater. 1 (2002) 59-63.
U. Schulz, "Review of modern techniques to generate antireflective propoerties on thermoplastic polymers", Appl. Opt. 45 (2006) 1608-1618.
B.E. Yoldas, D.P. Partlow, "Formation of Broad Band Antireflective Coatings on Fused Silica for High Power Laser Applications", Thin Solid Films 129 (1985) 1-14.
D. Chen, "Anti-reflection (AR) coatings made by sol-gel processes: A review", Sol. Energ. Mater. Sol. C. 68 (2001) 313-336.
M.F. Schubert, F.W. Mont, S. Chhajed, D.J. Poxson, J.K. Kim, E.F. Schubert, "Design of multilayer antireflection coatings made from co-sputtered and low-refractive-index materials by genetic algorithm", Opt. Exp. 16 (2008) 5290-5298.
H. Nagel, A. Metz, R. Hezel, "Porous SiO2 films prepared by remote plasma-enhanced chemical vapour deposition—a novel antireflection coating technology for photovoltaic modules", Sol. Energ. Mater. Sol. C. 65 (2001) 71-77.
Pfeiffer, Kristin, et al. "Antireflection coatings for strongly curved glass lenses by atomic layer deposition." Coatings 7.8 (2017): 118.
M. Sakhuja, J. Son, L.K. Verma, H. Yang, C.S. Bhatia, A.J. Danner, "Omnidirectional study of nanostructured glass packaging for solar modules", Prog. Photovol. 22 (2014) 356-361.
Metwalli, E., et al. "Surface characterizations of mono-, di-, and tri-aminosilane treated glass substrates." Journal of colloid and interface science 298.2 (2006): 825-831.
C.M. Kennemore Iii, U.J. Gibson, "Ion beam processing for coating MgF2 onto ambient temperature substrates", Appl. Opt. 23 (1984) 3608-3611.
D. Lee, M.F. Rubner, R.E. Cohen, "All-Nanoparticle Thin-Film Coatings", Nano Lett. 6 (2006) 2305-2312.
M. Kursawe, R. Anselmann, V. Hilarius, G. Pfaff, "Nano-Particles by Wet Chemical Processing in Commercial Applicaitons", J. Sol-Gel Sci. Technol. 33 (2005) 71-74.
Y. Zhao, U.S. Wang, G.Z. Mao, "Colloidal subwavelength nanostructures for anti reflection optical coatings", Opt. Lett. 30 (2005) 1885-1887.
D. Lee, Z. Gemici, M.F. Rubner, R.E. Cohen, "Multilayers of Oppositely Charged SiO2 Nanoparticles: Effect of Surface Charge on Multi9layer Assembly", Langmuir 23 (2007) 8833-8837.
K. Askar, B.M. Phillips, X. Dou, J. Lopez, C. Smith, B. Jiang, P. Jiang, "Self-assembled nanoparticle antiglare coatings", Opt. Lett. 37 (2012) 4380-4382.
H. Shimomura, Z. Gemici, R.E. Cohen, M.F. Rubner, "Layer-by-Layer-Assembled High-Performance Broadband Antireflection Coatings", ACS Appl. Mater. Interface 2 (2010) 813-820.
H.Y. Koo, D.K. Yi, S.J. Yoo, D.Y. Kim, "A Snowman-like Array of Colloidal Dimers for Antireflecting Surfaces**", Adv. Mater. 16 (2004) 274-277.
T. Lohmueller, M. Helgert, M. Sundermann, R. Brunner, J.P. Spatz, "Biomimetic Interfaces for High-Performance Optics in the Deep-UV Light Range", Nano Lett 8 (2008) 1429-1433.
M.S. Park, J.K. Kim, "Porous Structures of Polymer Films Prepared by Spin Coating with Mixed Solvents under Humid Condition", Langmuir 22 (2006) 4594-4598.
B.-T. Liu, Y.-T. Teng, R.-H. Lee, W.-C. Liaw, C.-H. Hsieh, "Strength of the interactions between light-scattering particles and resins affects the haze of anti-glare films", Colloid Surf. A 389 (2011) 138-143.
J.Q. Xi, M.F. Schubert, J.K. Kim, E.F. Schubert, M. Chen, S.-Y. Lin, LiuW, J.A. Smart, "Optical thin-film materials with low refractive index for broadband elimination of Fresnel reflection", Nat. Photon. 1 (2007) 176-179.

G.M. Nogueira, D. Banerjee, R.E. Cohen, M.F. Rubner, "Spray-Layer-by-Layer Assembly Can More Rapidly Produce Optical-Quality Multistack Heterostructures", Langmuir 27 (2011) 7860-7867.
C.S. Thompson, R.A. Fleming, M. Zou, "Solar Energy Materials & Solar Cells", Sol Energ Mater Sol C 115 (2013) 108-113.
G. Zhou, J. He, J. "Antireflective coatings on Fresnel lenses by spin-coating of solid silica nanoparticles", Nanosci. Nanotechnol. 13 (2013) Abstract.
J.-H. Kim, S. Fujita, S. Shiratori, "Design of a thin film for optical applications, consisting of high and low refractive index multilayers, fabricated by a layer-by-layer self-assembly method", Colloid Surf. Aspects 284-285 (2006) 290-294.
M.I. Dafinone, G. Feng, T. Brugarolas, K.E. Tettey, D. Lee, "Mechanical Reinforcement of Nanoparticle Thin Films Using Atomic Layer Deposition", ACS Nano 5 (2011) 5078-5087.
B.G. Prevo, E.W. Hon, O.D. Velev, "Assembly and characterization of colloid-based antireflective coatings on multicrystalline silicon solar cells", J. Mater. Chem. 17 (2007) 791-799.
B.G. Prevo, O.D. Velev, "Controlled, Rapid Deposition of Structured Coatings from Micro-and Nanoparticle Suspensions", Langmuir 20 (2004) 2099-2107.
H. Jiang, K. Yu, Y.C. Wang, "Antireflective structures via spin casting of polymer latex", Opt. Lett. 32 (2007) 575-577.
B.T. Liu, W.D. Yeh, "Reflective properties of nanoparticle-arrayed surfaces", Thin Solid Films 518 (2010) 6015-6021.
B.T. Liu, W.D. Yeh, "Antireflective surface fabricated from colloidal silica nanoparticles", Colloid Surf. A 356 (2010) 145-149.
A. Deak, I. Szekely, E. Kalman, Z. Keresztes, A.L. Kovacs, Z. Horvolgyi, "Nanostructured silica Langmuir-Blodgett films with antireflective properties prepared on glass substrates", Thin Solid Films 484 (2005) 310-317.
A. Deak, B. Bancsi, A.L. Toth, A.L. Kovacs, Z. Horvolgyi, "Complex Langmuir-Blodgett films from silica nanoparticles: An optical spectroscopy study", Colloid Surf. A 278 (2006) 10-16.
K.M. Yeung, W.C. Luk, K.C. Tam, C.Y. Kwong, M.A. Tsai, H.C. Kuo, A.M.C. Ng, A.B. Djurisic, "2-Step self-assembly method to fabricate broadband omnidirectional antireflection coating in large scale", Sol Energ Mater Sol C 95 (2011) 699-703.
X. Li, O. Niitsoo, A. Couzis, "Electrostatically driven adsorption of silica nanoparticles on functionalized surfaces", J. Colloid Interf. Sci. 394 (2013) 26-35.
X. Li, O. Niitsoo, A. Couzis, "Experimental studies on irreversibility of electrostatic adsorption of silica nanoparticles at solid-liquid interface", J. Colloid Interf. Sci. 420 (2014) 50-56.
H. Fudouzi, M. Kobayashi, N. Shinya, "Assembly of Microsized Colloidal Particles on Electrostatic Regions Patterned through Ion Beam Irradiation", Langmuir 18 (2002) 7648-7652.
Y. Masuda, M. Itoh, T. Yonezawa, K. Koumoto, "Low-Dimensional Arrangement of SiO2 Particles", Langmuir 18 (2002) 4155-4159.
J. Tien, A. Terfort, G.M. Whitesides, "Microfabrication through Electrostatic Self-Assembly", Langmuir 13 (1997) 5349-5355.
S. Degand, G. Lamblin, C.C. Dupont-Gillain, "Colloidal lithography using silica particles: Improved particle distribution and tunable wetting properties", J. Colloid Interf. Sci. 392 (2013) 219-225.
J. Aizenberg, P.V. Braun, P. Wiltzius, "Patterned Colloidal Deposition Controlled by Electrostatic and Capillary Forces", Phys. Rev. Lett. 84 (2000) 2997-3000.
X.T. Zhang, O. Sato, M. Taguchi, Y. Einaga, T. Murakami, A. Fujishima, "Self-Cleaning Particle Coating with Antireflection Properties", Chem. Mater. 17 (2005) 696-700.
S.P. Pack, N.K. Kamisetty, M. Nonogawa, K.C. Devarayapalli, K. Ohtani, K. Yamada, Y. Yoshida, T. Kodaki, K. Makino, "Direct immobilization of DNA oligomers onto the amine-functionalized glass surface for DNA microarray fabrication through the activation-free reaction of oxanine", Nucleic Acids Res. 35 (2007), 10 pages.
M.G. Moharam, D.A. Pommet, E.B. Grann, T.K. Gaylord, "Stable implementation of the rigorous coupled-wave analysis for surface-relief gratings: enhanced transmittance matrix approuch", J. Opt. Soc. Am. A 12 (1995) 1077-1086.
W.L. Min, B. Jiang, P. Jiang, "Bioinspired Self-Cleaning Antireflection Coatings", Adv. Mater. 20 (2008) 3914-3918.

(56) References Cited

OTHER PUBLICATIONS

D.G. Stavenga; et al. "Light on the moth-eye corneal nipple array of butterflies", Proc. R. Soc. B 273 (2006) 661-667.

Yakacki, Christopher M., et al. "Impact of shape-memory programming on mechanically-driven recovery in polymers." Polymer 52.21 (2011): 4947-4954.

S. Lu,; et al. "Receptor-Ligand-Based Specific Cell Adhesion on Solid Surfaces: Hippocampal Neuronal Cells on Bilinker Functionalized Glass" Nano Lett. 6 (2006) 1977-1981.

B.T. Liu; et al. "A novel method to control inner and outer haze of an anti-glare film by surface modification of light-scattering particles", J. Colloid Interf. Sci. 350 (2010) 421-426.

Han, H; et al. "Metal-assisted chemical etching of silicon and nanotechnology applications" ScienceDirect 2014, 9, 271-304.

Lishchuk, P; et al. "Photoacoustic characterization of nanowire arrays formed by metal-assisted chemical etching of crystalline silicon substrates with different doping level" ScienceDirect 2019, 131-136.

Cao, Z; et al. "Study on the impact of silicon doping level on the trench profile using metal-assisted chemical etching" 2016, vol. 12, 742-746.

Toor, F; et al. "Nanostructured silicon via metal assisted catalyzed etch (MACE): chemistry fundamentals and pattern engineering" Nanotechnology 2016, 27, 412003.

Huang, Z; et al. "Metal-Assisted chemical etching of silicon: a review" Advanced Materials 2011, 23, 285-308.

Cansizoglu, H; et al. "Optical absorption properties of semiconducting nanostructures with different shapes" Advanced Optical Materials 2013, 1, 156-166. (Year: 2013).

Phillips; et al "Biomimetic broadband antireflection gratings on solar-grade multicrystalline silicon wafers" Applied Physics Letters; Nov. 9, 2011, vol. 99, pp. 191103 (1)-(3).

Sun; et al. "Broadband moth-eye antireflection coatings on silicon" Applied Physics Letters; Feb. 14, 2008, vol. 92, pp. 061112 (1)-(3).

Li, Y., et al. "Broadband near-infrared antireflection coatings fabricated by three-dimensional direct laser writing." Optics letters 43.2 (2018): 239-242.

Habault et al., "Light-triggered self-healing and shape-memory polymers", Chem. Soc. Rev. 2013, 42: 7244-7256.

Yakacki et al., "Shape-Memory Polymers for Biomedical Applications", Adv. Polym. Sci. 2010, 226:147-175.

T. Xie, "Recent advances in polymer shape memory", Polymer 2011, 52: 4985-5000.

Lendlein et al., "Shape-Memory Effect"—From temporary shape . . . T>46 ° C . . . to permanent shape, Angew. Chem. Int. Ed. 2002, 41: 2034-2057.

Liu et al., "Review of progress in shape-memory polymers", J. Mater. Chem., 2007, 17: 1543-1558.

Meng et al., "A Brief Review of Stimulus-active Polymers Responsive to Thermal, Light, Magnetic, Electric, and Water/Solvent Stimuli", Journal of Intelligent Material Systems and Structures, vol. 21—Jun. 2010: 859-885.

Nguyen et al., "Modeling the Relaxation Mechanisms of Amorphous Shape Memory Polymers", M. L. Chambers, Adv. Mater. 2010, 22: 3411-3423.

Stuart et al., "Emerging applications of stimuli-responsive polymer materials", Nature Materials 2010, 9: 101-113.

C. Yakacki, "Shape-Memory and Shape-Changing Polymers", Polymer Reviews, 2013, 53: 1-5.

Kloxin et al., "Covalent adaptable networks: smart, reconfigurable and responsive network systems", Chem. Soc. Rev. 2013, 42: 7161-7173.

Behl et al., "Multifunctional Shape-Memory Polymers", Adv. Mater. 2010, 22: 3388-3410.

L. Ionov, "3D Microfabrication using Stimuli-Responsive Self-Folding Polymer Films", Polymer Reviews, 2013, 53: 92-107.

Felton et al., Soft Matter "Self-folding with shape memory composites", Soft Matter, 2013, 9, 7688-7694.

Gugliuzza et al., "A reviewon membrane engineering for innovation in wearable fabrics and protective textiles", Journal of Membrane Science 446(2013): 350-375.

Leng et al., "Shape-Memory Polymers—A Class of Novel Smart Materials", MRS Bulletin 2009, 34: 848-855, www.mrs.org/bulletin.

Metzger et al., "Mechanical Properties of Mechanical Actuator for Treating Ischemic Stroke", Biomedical Microdevices 2002, 4:2: 89-96.

Small IV, et al., "Laser-activated shape memory polymer intravascular thrombectomy device", Optics Express 2005, 13: 8204-8213.

Tobushi et al., "Thermomechanical properties in a thin film of shape memory polymer of polyurethane series", Smart Mater. Struct. (1996) 5: 483-491.

Lendlein et al., "Biodegradable, Elastic Shape-Memory Polymers for Potential Biomedical Applications", Science 2002, vol. 296: 1673-1676.

Xue et al., "Synthesis and characterization of elastic star shape-memory polymers as self-expandable drug-eluting stents", Journal of Materials Chemistry 2012, 22: 7403-7411.

Yakacki et al., "Unconstrained recovery characterization of shape-memory polymer networks for cardiovascular applications", ScienceDirect, Biomaterials 2007, 28: 2255-2263.

Maitland et al., "Photothermal Properties of Shape Memory Polymer Micro-Actuators for Treating Stroke", Lasers in Surgery and Medicine (2002) 30:1-11.

Leng et al., "Synergic effect of carbon black and short carbon fiber on shape memory polymer actuation by electricity", Journal of Applied Physics 2008, 104: 1-4.

Koerner et al., "Remotely actuated polymer nanocomposites—stress-recovery of carbon-nanotube-filled thermoplastic elastomers", nature materials 2004, 3: 115-120.

Yang et al., "Macroporous photonic crystal-based vapor detectors created by doctor blade coating", Appl. Phys. Lett. 2011, 98: 1-3.

Meng et al., "Various shape memory effects of stimuli-responsive shape memory polymers", Smart Materials and Structures 2013, 22: 1-23.

Mather et al., "Shape Memory Polymer Research", Annu. Rev. Mater. Res. 2009. 39: 445-471.

Heuwers et al., "Shape-Memory Natural Rubber: An Exceptional Material for Strain and Energy Storage", Macromolecular Chemistry and Physics 2013, 214: 912-923.

Heuwers et al., "Stress-Induced Stabilization of Crystals in Shape Memory Natural Rubber", Macromolecular Rapid Communications 2013, 34: 180-184.

Xie et al., "Encoding Localized Strain History Through Wrinkle Based Structural Colors", Advanced Materials 2010, 22: 1390-4394.

Xu et al., "Deformable, Programmable, and Shape-Memorizing Micro-Optics", Advanced Functional Materials 2013, 23: 3299-3306.

Kunzelman et al., "Shape memory polymers with built-in threshold temperature sensors", Journal of Materials Chemistry 2008, 18: 1082-1086.

Lv et al., "Shape-Memory Polymer in Response to Solution", Advanced Engineering Materials 2008, 10, No. 6: 592-595.

Huang et al., "Water-driven programmable polyurethane shape memory polymer: Demonstration and mechanism", Applied Physics Letters 2005, 86: 1-3.

Du et al., "Solvent induced shape recovery of shape memory polymer based on chemically cross-linked poly(vinyl alcohol)", Soft Matter, 2010, 6: 3370-3376.

Gu et al., "Water-triggered shape memory of multiblock thermoplastic polyurethanes (TPUs)", RSC Adv. 2013, 3: 15783-15791.

Quitmann et al., "Environmental Memory of Polymer Networks under Stress", Adv. Mater. 2014, 26: 3441-3444.

Ding et al., "Morphology and Water Vapor Permeability of Temperature-Sensitive Polyurethanes", Journal of Applied Polymer Science, (2008) vol. 107: 4061-4069.

Witt, Kendhl Kate. "Optical Sensors for the Analysis of Alcohols in Fuels." (2016).

Fenzl et al., "Photonic Crystals for Chemical Sensing and Biosensing", Angewandte Chemie Ed. 2015, 53: 3318-3335.

(56) References Cited

OTHER PUBLICATIONS

Hatton et al., "Assembly of large-area, highly ordered, crack-free inverse opal films", PNAS 2010, vol. 107, 23: 10354-10359.
Weissman et al., "Thermally Switchable Periodicities and Diffraction from Mesoscopically Ordered Materials", Science 1996, 274: 959-960.
Mao, D.; et al. Design of Nano-Opto-Mechanical Reconfigurable Photonic Integrated Circuit. J. Lightwave Technol. 2013, 31, 1660-1669.
Park, H. G.; et al. Electrically Driven Single-Cell Photonic Crystal Laser. Science 2004, 305, 1444-1447.
Hu, H.; et al. Photonic Anti-Counterfeiting Using Structural Colors Derived from Magnetic-Responsive Photonic Crystals with Double Photonic Bandgap Heterostructures. J. Mater. Chem. 2012, 22, 11048-11053.
Cho, Y.; et al. Elastoplastic Inverse Opals as Power-Free Mechanochromic Sensors for Force Recording. Adv. Funct. Mater. 2015, 25, 6041-6049.
Heo, Y.; et al. Controlled Insertion of Planar Defect in Inverse Opals for Anticounterfeiting Applications. ACS Appl. Mater. Interfaces 2017, 9, 43098-43104.
Hou, J.; et al. Four-Dimensional Screening Anti-Counterfeiting Pattern by Inkjet Printed Photonic Crystals. Chem.—An Asian J. 2016, 11, 2680-2685.
Yang, D. P.; et al. Polymerization-Induced Colloidal Assembly and Photonic Crystal Multilayer for Coding and Decoding. Adv. Funct. Mater. 2014, 24, 817-825.
Lee, H. S.; et al. Colloidal Photonic Crystals toward Structural Color Palettes for Security Materials. Chem. Mater. 2013, 25, 2684-2690.
Shang, S. L.; et al. Fabrication of Magnetic Field Induced Structural Colored Films with Tunable Colors and Its Application on Security Materials. J. Colloid Interface Sci. 2017, 485, 18-24.
Peng, C. Y.; et al. Flexible Photonic Crystal Material for Multiple Anticounterfeiting Applications. ACS Appl. Mater. Interfaces 2018, 10, 9858-9864.
Keller, K.; et al. Inkjet Printing of Multicolor Daylight Visible Opal Holography. Adv. Funct. Mater. 2018, 28, 1706903.
Wu, S. L.; et al. Structural Color Patterns on Paper Fabricated by Inkjet Printer and Their Application in Anticounterfeiting. J. Phys. Chem. Lett. 2017, 8, 2835-2841.
Meng, Y.; et al. Patterned and Iridescent Plastics with 3d Inverse Opal Structure for Anticounterfeiting of the Banknotes. Adv. Opt. Mater. 2018, 6, 1701351.
Lee, E.; et al. Bio-Inspired Responsive Polymer Pillar Arrays. MRS Commun. 2015, 5, 97-114.
Meng, Z. P.; et al. Structurally Colored Polymer Films with Narrow Stop Band, High Angle-Dependence and Good Mechanical Robustness for Trademark Anti-Counterfeiting. Nanoscale 2018, 10, 14755-14762.
Wang, M. S.; et al. Magnetically Responsive Nanostructures with Tunable Optical Properties. J. Am. Chem. Soc. 2016, 138, 6315-6323.
Han, M. G.; et al. Full Color Tunable Photonic Crystal from Crystalline Colloidal Arrays with an Engineered Photonic Stop-Band. Adv. Mater. 2012, 24, 6438-6444.
Ge, J. P.; et al. Responsive Photonic Crystals. Angew. Chem. Int. Ed. 2011, 50, 1492-1522.
Heo, Y.; et al. Lithographically Encrypted Inverse Opals for Anti-Counterfeiting Applications. Small 2016, 12, 3819-3826.
Zhong, K.; et al. Instantaneous, Simple, and Reversible Revealing of Invisible Patterns Encrypted in Robust Hollow Sphere Colloidal Photonic Crystals. Adv. Mater. 2018, 30, 1707246.
Burgess, I. B.; et al. Encoding Complex Wettability Patterns in Chemically Functionalized 3d Photonic Crystals. J. Am. Chem. Soc. 2011, 133, 12430-12432.
Hu, H. B.; et al. Magnetically Responsive Photonic Watermarks on Banknotes. J. Mater. Chem. C 2014, 2, 3695-3702.
Ding, T.; et al. Revealing Invisible Photonic Inscriptions: Images from Strain. ACS Appl. Mater. Interfaces 2015, 7, 13497-13502.

Nam, H.; et al. Inkjet Printing Based Mono-Layered Photonic Crystal Patterning for Anti-Counterfeiting Structural Colors. Sci. Rep. 2016, 6, 30885.
Lendlein, A.; et al. Shape-Memory Polymers. Angew. Chem. Int. Ed. 2002, 41, 2034-2057.
Zhao, Q.; et al. Shape Memory Polymer Network with Thermally Distinct Elasticity and Plasticity. Sci. Adv. 2016, 2, e1501297.
Zhao, Q.; et al. Recent Progress in Shape Memory Polymer: New Behavior, Enabling Materials, and Mechanistic Understanding. Prog. Polym. Sci. 2015, 49-50, 79-120.
Zhang, G. G.; et al. Unusual Aspects of Supramolecular Networks: Plasticity to Elasticity, Ultrasoft Shape Memory, and Dynamic Mechanical Properties. Adv. Funct. Mater. 2016, 26, 931-937.
Mather, P. T.; et al. Shape Memory Polymer Research. Annu. Rev. Mater. Res. 2009, 39, 445-471.
Schauer, S.; et al. Tunable Diffractive Optical Elements Based on Shape-Memory Polymers Fabricated via Hot Embossing. ACS Appl. Mater. Interfaces 2016, 8, 9423-9430.
Li, P.; et al. Novel Programmable Shape Memory Polystyrene Film: A Thermally Induced Beam-Power Splitter. Sci. Rep. 2017, 7, 44333.
Moirangthem, M.; et al. Photonic Shape Memory Polymer with Stable Multiple Colors. ACS Appl. Mater. Interface 2017, 9, 32161-32167.
Moirangthem, M.; et al. An Optical Sensor Based on a Photonic Polymer Film to Detect Calcium in Serum. Adv. Funct. Mater. 2016, 26, 1154-1160.
Fang, Y.; et al. Chromogenic Photonic Crystals Enabled by Novel Vapor-Responsive Shape Memory Polymers. Adv. Mater. 2015, 27, 3696-3704.
Fang, Y.; et al. Reconfigurable Photonic Crystals Enabled by Multistimuli-Responsive Shape Memory Polymers Possessing Room Temperature Shape Processability. ACS Appl. Mater. Interfaces 2017, 9, 5457-5467.
Leo, S. Y.; et al. Chromogenic Photonic Crystal Sensors Enabled by Multistimuli-Responsive Shape Memory Polymers. Small 2018, 14, 1703515.
Stöber, W.; et al. Controlled Growth of Monodisperse Silica Spheres in Micron Size Range. J. Colloid Interface Sci. 1968, 26, 62-69.
Schneider, Friedrich. "The financial flows of transnational crime and tax fraud in OECD countries: What do we (not) know?." Public Finance Review 41.5 (2013): 677-707.
Mittleman, D. M.; et al. Optical Properties of Planar Colloidal Crystals: Dynamical Diffraction and the Scalar Wave Approximation. J. Chem. Phys. 1999, 111, 345-354.
Yunus, S.; et al. Diffusion of Oligomers from Polydimethylsiloxane Stamps in Microcontact Printing: Surface Analysis and Possible Application. Surf. Interface Anal. 2007, 39, 922-925.
McDonald, J. C.; et al. Poly(Dimethylsiloxane) as a Material for Fabricating Microfluidic Devices. Acc. Chem. Res. 2002, 35, 491-499.
Dangla, R.; et al. Microchannel Deformations Due to Solvent-Induced Pdms Swelling. Lab Chip 2010, 10, 2972-2978.
Lee, J. N.; et al. Solvent Compatibility of Poly(Dimethylsiloxane)-Based Microfluidic Devices. Anal. Chem. 2003, 75, 6544-6554.
Mata, A.; et al. Characterization of Polydimethylsiloxane (Pdms) Properties for Biomedical Micro/Nanosystems. Biomed. Microdevices 2005, 7, 281-293.
Stojilovic, N., Why Can't We See Hydrogen in X-Ray Photoelectron Spectroscopy? J. Chem. Edu. 2012, 89, 1331-1332.
Louette, P.; et al. Poly(Dimethyl Siloxane) (Pdms) Xps Reference Core Level and Energy Loss Spectra Surf. Sci. Spectra 2006, 12, 38-43.
Li, H. L.; et al. Superoleophilic and Superhydrophobic Inverse Opals for Oil Sensors. Adv. Funct. Mater. 2008, 18, 3258-3264.
Park, Wounjhang; et al. "Mechanically tunable photonic crystal structure." Applied Physics Letters 85.21 (2004): 4845-4847.
Joannopoulos, J. D.; et al. Photonic Crystals: Molding the Flow of Light. Princeton University Press: Princeton, 1995.
Mohr, Gerhard J., Daniel Citterio, and Ursula E. Spichiger-Keller. "Development of chromogenic reactands for optical sensing of alcohols." Sensors and Actuators B: Chemical 49.3 (1998): 226-234.

(56) References Cited

OTHER PUBLICATIONS

International Search Report and Written Opinion dated Jun. 26, 2012 for PCT Patent Application No. PCT/US2011/057484.
International Preliminary Report on Patentability dated May 10, 2013 for PCT Patent Application No. PCT/US2011/057484.
Munakata, et al., Three-dimensionally ordered macroporous polyimide composite membrane with controlled pore size for direct methanol fuel cells, Journal of Power Sources 2008, 178(2): 596-602.
Woo et al., Preparation and characterization of three dimensionally ordered macroporous Li4Ti5O12 anode for lithium batteries, Electrochimica Acta 2007, 53(1): 79-82.
Jiang et al., Template-Directed Preparation of Macroporous Polymers with Oriented and Crystalline Arrays of Voids, Journal of the American Chemical Society 1999, 121(50): 11630-11637.
Kluhr et al., Partially Oxidized Macroporous Silicon: A Three-Dimensional Photonic Matrix for Microarray Applications, Advanced Materials 2006, 18(23): 3135-3139.
Zhang et al., Fabrication and bioseparation studies of adsorptive membranes/felts made from electrospun cellulose acetate nanofibers, Journal of Membrane Science 2008, 319(1-2):176-184.
Grigoras et al., Fabrication of porous membrane filter from p-type silicon, Physica Status Solidi 2005 (a) 202(8): 1624-1628.
International Search Report for PCT/US19/38193 dated Sep. 5, 2019.
Aksoy, Gökhan, et al. "Effect of various treatment and glazing (coating) techniques on the roughness and wettability of ceramic dental restorative surfaces." Colloids and surfaces B: Biointerfaces 53.2 (2006): 254-259.
Al-Marzok, Maan; et al. "The effect of the surface roughness of porcelain on the adhesion of oral *Streptococcus mutans*." J Contemp Dent Pract 10.6 (2009): E017-24.
Bartlett, D. W., et al. "The association of tooth wear, diet and dietary habits in adults aged 18-30 years old." Journal of dentistry 39.12 (2011): 811-816.
Butler, Craig J., et al. "Effect of fluoride and 10% carbamide peroxide on the surface roughness of low-fusing and ultra low-fusing porcelain." The Journal of prosthetic dentistry 92.2 (2004): 179-183.
Ccahuana, Vanessa ZS, et al. "Surface degradation of glass ceramics after exposure to acidulated phosphate fluoride." Journal of Applied Oral Science 18.2 (2010): 155-165.
Creugers, Nico HJ; et al. "A meta-analysis of durability data on conventional fixed bridges." Community Dentistry and Oral Epidemiology 22.6 (1994): 448-452.
Drummond, J. L., D; et al. "Physiological aging of an all-ceramic restorative material." Dental Materials 7.2 (1991): 133-137.
Esquivel-Upshaw, Josephine, et al. "Randomized, controlled clinical trial of bilayer ceramic and metal-ceramic crown performance." Journal of Prosthodontics: Implant, Esthetic and Reconstructive Dentistry 22.3 (2013): 166-173.
Esquivel-Upshaw, Josephine F., et al. "Resistance to staining, flexural strength, and chemical solubility of core porcelains for all-ceramic crowns." International Journal of Prosthodontics 14.3 (2001).
Esquivel-Upshaw, Josephine F., et al. "In Vivo Wear of Enamel by a Lithia Disilicate-Based Core Ceramic Used for Posterior Fixed Partial Dentures: First-Year Results." International Journal of Prosthodontics 19.4 (2006).
Esquivel-Upshaw, J. F., et al. "Surface degradation of dental ceramics as a function of environmental pH." Journal of dental research 92.5 (2013): 467-471.
Ionov, Leonid. "Soft microorigami: self-folding polymer films." Soft Matter 7.15 (2011): 6786-6791.
Fischer, H.; et al. "Effect of surface roughness on flexural strength of veneer ceramics." Journal of Dental Research 32.12 (2003): 972-975.
Flannery, Anthony F., et al. "PECVD silicon carbide as a chemically resistant material for micromachined transducers." Sensors and Actuators A: Physical 70.1-2 (1998): 48-55.

Zhang, Haixia, et al. "Application of PECVD SiC in glass micromachining." Journal of Micromechanics and Microengineering 17.4 (2007): 775.
Heintze, Siegward D; et al. "Survival of zirconia-and metal-supported fixed dental prostheses: a systematic review." International Journal of Prosthodontics 23.6 (2010).
Herrmann, M., et al. "Corrosion of silicon nitride materials in acidic and basic solutions and under hydrothermal conditions." Journal of the European Ceramic Society 23.4 (2003): 585-594.
Herrmann, M. "Corrosion of silicon nitride materials in aqueous solutions." Journal of the American Ceramic Society 96.10 (2013): 3009-3022.
Ogawa, Yudai, et al. "Organic transdermal iontophoresis patch with built-in biofuel cell." Advanced healthcare materials 4.4 (2015): 506-510.
Kukiattrakoon, Boonlert; et al. "Vicker's microhardness and energy dispersive x-ray analysis of fluorapatite-leucite and fluorapatite ceramics cyclically immersed in acidic agents." Journal of oral science 51.3 (2009): 443-450.
Kukiattrakoon, Boonlert; et al. "The effect of acidic agents on surface ion leaching and surface characteristics of dental porcelains." The journal of prosthetic dentistry 103.3 (2010): 148-162.
Kukiattrakoon, Boonlert; et al. "Degradability of fluorapatite-leucite ceramics in naturally acidic agents." Dental materials journal (2010): 1008310070-1008310070.
Kukiattrakoon, Boonlert; et al. "Chemical durability and microhardness of dental ceramics immersed in acidic agents." Acta Odontologica Scandinavica 68.1 (2010): 1-10.
Kukiattrakoon, Boonlert; et al. "Effect of acidic agents on surface roughness of dental ceramics." Dental research journal 8.1 (2011): 6.
Milleding, Percy, et al. "Surface energy of non-corroded and corroded dental ceramic materials before and after contact with salivary proteins." European journal of oral sciences 107.5 (1999): 384-392.
Miyazaki, Takashi, et al. "Current status of zirconia restoration." Journal of prosthodontic research 57.4 (2013): 236-261.
Pinto, Marcelo M., et al. "Influence of pH on slow crack growth of dental porcelains." dental materials 24.6 (2008): 314-823.
Preis, Verena, et al. "Wear performance of dental ceramics after grinding and polishing treatments." Journal of the mechanical behavior of biomedical materials 10 (2012): 13-22.
Raigrodski, Ariel J.; et al. "The safety and efficacy of anterior ceramic fixed partial dentures: a review of the literature." The journal of prosthetic dentistry 86.5 (2001): 520-525.
Rosenstiel, S. F., et al. "Strength of a dental glass-ceramic after surface coating." Dental Materials 9.4 (1993): 274-279.
Sailer, Irena, et al. "A systematic review of the survival and complication rates of all-ceramic and metal-ceramic reconstructions after an observation period of at least 3 years. Part II: fixed dental prostheses." Clinical oral implants research 18 (2007): 86-96.
Salido, María P., et al. "Prospective clinical study of zirconia-based posterior four-unit fixed dental prostheses: four-year follow-up." International Journal of Prosthodontics 25.4 (2012).
Scurria, Mark S.; et al. "Meta-analysis of fixed partial denture survival: prostheses and abutments." The Journal of prosthetic dentistry 79.4 (1998): 459-464.
Karrock, Torben; et al. "Pressure sensor based on flexible photonic crystal membrane." Biomedical optics express 6.12 (2015): 4901-4911.
International Search Report and Written Opinion issued in PCT/US2017/046886 dated Oct. 20, 2017.
International Search Report and Written Opinion for PCT/US2014/063163 dated Jun. 25, 2015.
S. Walheim, E. Schäffer, J. Mlynek, U. Steiner, "Nanophase-Separated Polymer Films as High-Performance Antireflection Coatings", Science 283 (1999) 520-522.
A. Gombert, W. Glaubitt, K. Rose, J. Dreibholz, B. Bläsi, A. Heinzel, D. Sporn, W. Döll, V. Wittwer, "Subwavelength-structured antireflective surfaces on glass", Thin Solid Films 351 (1999) 73-78.
C. Heine, R.H. Morf, "Submicrometer gratings for solar energy applications", Appl. Opt. 34 (1995) 2476-2482.

(56) References Cited

OTHER PUBLICATIONS

M. Ibn-Elhaj, M. Schadt, "Optical polymer thin films with isotropic and anisotropic nano-corrugated surface topologies", Nature 410 (2001) 796-799.
A. Gombert, B. Blasi, C. Buhler, P. Nitz, J. Mick, W. Hossfeld, M. Niggemann, "Some application cases and related manufacturing techniques for optically functional microstructures on large areas", Opt. Eng. 43 (2004) 2525-2533.
J. D. Joannopoulos, R. D. Meade, J. N. Winn, Photonic Crystals: Molding the Flow of Light, Princeton University Press, 135 pages.
A. Lendlein, "Shape-Memory Polymers", Advances in Polymer Science 226, Springer, New York, NY 2010, 1-209.
A. Luque, S. Hegedus, Handbook of Photovoltaic Science and Engineering. John Wiley & Sons, West Sussex, 2003, 115 pages.
H.A. Macleod, Thin-Film Optical Filters. Third ed., Institute of Physics Publishing, Bristol, 2001, 666 pages.
Gregg, S. J.; et al. Adsorption, Surface Area and Porosity. 2nd ed.; Academic Press Inc.: London, 1982.
Arsenault et al., "From colour fingerprinting to the control of photoluminescence in elastic photonic crystals", nature materials 2006, 5: 179-184.
Kang et al., "Broad-wavelength-range chemically tunable block-copolymer photonic gels", Nature Materials 2007, 6: 957-960.
Fudouzi et al., "Colloidal Crystals with Tunable Colors and Their Use as Photonic Papers", Langmuir 2003, 19: 9653-9660.
Ge et al., "Rewritable Photonic Paper with Hygroscopic Salt Solution as Ink", Advanced Materials 2009, 21: 4259-4264.
Jang et al., "Combining Pattern Instability and Shape-Memory Hysteresis for Phononic Switching", Nano Lett. 2009, 9, 5: 2113-2119.
Takeoka et al., "Polymer Gels that Memorize Structures of Mesoscopically Sized Templates. Dynamic and Optical Mature of Periodic Ordered Mesoporous Chemical Gels", Langmuir 2002, 18: 5977-5980.
Ge et al., "Highly Tunable Superparamagnetic Colloidal Photonic Crystals", Angew. Chem. Int. Ed. 2007, 46: 7428-7431.
Chan et al., "Mechanochromic Photonic Gels", Advanced Materials 2013, 25: 3934-3947.
Pan et al., "Response of inverse-opal hydrogels to alcohols", Journal of Materials Chemistry 2012, 22: 2018-2025.
Burgess et al., "Structural colour in colourimetric sensors and indicators", Journal of Materials Chemistry C 2013, 1: 6075-6086.
Yue et al., "Mechano-actuated ultrafast full-colour switching in layered photonic hydrogels", nature communications 2014: 1-8.
Yue et al., "Lamellar Hydrogels with High Toughness and Ternary Tunable Photonic Stop-Band", Advanced Materials 2013, 25: 3106-3110.
Cui et al., "Inverse Opal Spheres Based on Polyionic Liquids as Functional Microspheres with Tunable Optical Properties and Molecular Recognition Capabilities", Angew. Chem. Int. Ed. 2014, 53: 3844-3848.
Han et al., "Full Color Tunable Photonic Crystal from Crystalline Colloidal Arrays with an Engineered Photonic Stop-Band", Adv. Mater. 2012, 24,: 6438-6444.
Yang et al., "From Metastable Colloidal Crystalline Arrays to Fast Responsive Mechanochromic Photonic Gels: An Organic Gel for Deformation-Based Display Panels", Adv. Funct. Mater. 2014, 24: 3197-3205.
Ye et al., "Invisible Photonic Prints Shown by Deformation", Advanced Functional Materials 2014, 24: 6430-6438.
Asher et al., "Photonic Crystal Carbohydrate Sensors: Low Ionic Strength Sugar Sensing", J. Am. Chem. Soc. 2003, 125: 3322-3329.
Holtz et al., "Polymerized colloidal crystal hydrogel films as intelligent chemical sensing materials", Nature 1997, 389: 829-832.
Schäfer et al., "Reversible Light-, Thermo-, and Mechano-Responsive Elastomeric Polymer Opal Films", Chemistry of Materials 2013, 25: 2309-2318.
Schäfer et al., "Fully Reversible Shape Transition of Soft Spheres in Elastomeric Polymer Opal Films", Langmuir 2013, 29: 11275-11283.

Fang et al., "Reconfigurable photonic crystals enabled by pressure-responsive shape-memory polymers", Nature Communications 2015: 1-8.
Velev et al., "Porous silica via colloidal crystallization", Nature 1997, 389: 447-448.
Jiang et al., "Template-Directed Preparation of Macroporous Polymers with Oriented and Crystalline Arrays of Voids", J. Am. Chem. Soc. 1999, 121: 11630-11637.
Tsai et al., "Retainment of pore connectivity in membranes prepared with vapor-induced phase separation", Journal of Membrane Science 2010, 362: 360-373.
Mason et al., "Correlation between bulk morphology and luminescence in porous silicon investigated by pore collapse resulting from drying", Thin Solid Films 2002, 406: 151-158.
Bertone et al., "Thickness Dependence of the Optical Properties of Ordered Silica-Air and Air-Polymer Photonic Crystals", Physical Review Letters 1999, 83, 2: 300-303.
Gemici et al., "Targeted Functionalization of Nanoparticle Thin Films via Capillary Condensation", Nano Letters 2009, 9, 3: 1064-1070.
Potyrailo et al., "Morpho butterfly wing scales demonstrate highly selective vapour response", Nature photonics 2007, 1: 123-128.
Kobatake; et al. "Rapid and reversible shape changes of molecular crystals on photoirradiation" vol. 446, Apr. 12, 2007, doi: 10.1038/nature05669, pp. 1-4.
Han, Moon Gyu, et al. "Full color tunable photonic crystal from crystalline colloidal arrays with an engineered photonic stop-band." Advanced Materials 24.48 (2012): 6438-6444.
Gourevich, Ilya, et al. "Multidye nanostructured material for optical data storage and security labeling." Chemistry of materials 16.8 (2004): 1472-1479.
International Search Report for PCT/US2018/066349 dated Mar. 15, 2019.
International Search Report for PCT/US2018/066353 dated Mar. 15, 2019.
International Search Report for PCT/US2018/066234 dated Mar. 25, 2019.
"Light" Wikipedia https://en.wikipedia.orgiwiindex.php?title=Light &oldid=797818857 (accessed Feb. 22, 2019).
"Using polyimide tape to mask against reactive-ion etching" Tech Briefs, 2002 (accessed Feb. 22, 2019).
Chen; et al. "Directed water shedding on high-aspect-ratio shape memory polymer micropillar arrays" Advanced Materials, 2014, pp. 1283-1288, vol. 26, doi: 10.1002/adma.201304030.
International Search Report for International Application No. PCT/US2019/017862, dated Jan. 21, 2020.
Yoon, B.; et al., Recent Functional Material Based Approaches to Prevent and Detect Counterfeiting. J. Mater. Chem. C 2013, 1, 2388-2403.
Wang, Zhen, et al. "Programmable, pattern-memorizing polymer surface." Advanced Materials 23.32 (2011): 3669-3673.
Pham, H. H.; et al. Multidye Nanostructured Material for Optical Data Storage and Security Data Encryption. Adv. Mater. 2004, 16, 516-520.
Zhao, Y.; et al Bio-Inspired Variable Structural Color Materials. Chem. Soc. Rev. 2012, 41, 3297-3317.
Fu, Q. Q.; et al. Hierarchically Structured Photonic Crystals for Integrated Chemical Separation and Colorimetric Detection Nanoscale 2017, 9, 2457-2463.
Lv, T.;; et al. Superhydrophobic Surface with Shape Memory Micro/Nanostructure and Its Application in Rewritable Chip for Droplet Storage. ACS Nano 2016, 10, 9379-9386.
Aguirre, C. I.; et al. Tunable Colors in Opals and Inverse Opal Photonic Crystals. Adv. Funct. Mater. 2010, 20, 2565-2578.
Boyle, B. M.; et al. Structural Color for Additive Manufacturing: 3d-Printed Photonic Crystals from Block Copolymers. ACS Nano 2017, 11, 3052-3058.
Velev, O. D.; et al. Materials Fabricated by Micro- and Nanoparticle Assembly—the Challenging Path from Science to Engineering. Adv. Mater. 2009, 21, 1897-1905.
Cai, Z. Y.; et al. A Photonic Crystal Protein Hydrogel Sensor for Candida Albicans. Angew. Chem. Int. Ed. 2015, 54, 13036-13040.

(56) References Cited

OTHER PUBLICATIONS

Kuznetsov, A. I.; et al. Optically Resonant Dielectric Nanostructures. Science 2016, 354, 2472.
Vlasov, Y. A.; et al. On-Chip Natural Assembly of Silicon Photonic Bandgap Crystals. Nature 2001, 414, 289-293.

* cited by examiner

METHODS AND SENSORS FOR DETECTION

This application is a continuation of U.S. application Ser. No. 16/611,745 filed on Nov. 7, 2019, which application is the 35 U.S.C. § 371 national stage of PCT application having serial number PCT/US2018/033173, filed on May 17, 2018. This application also claims the benefit of and priority to U.S. Provisional Application Ser. No. 62/507,294, having the title "METHODS AND SENSORS FOR DETECTION," filed on May 17, 2017, the disclosure of which is incorporated herein in by reference in its entirety.

FEDERAL SPONSORSHIP

This invention was made with government support under HDTRA1-15-1-0022 awarded by Defense Threat Reduction Agency. The government has certain rights in the invention.

This invention was made with government support under CMMI-1562861 awarded by the National Science Foundation. The government has certain rights in the invention.

BACKGROUND

Detection of liquid phase chemical such as ethanol, acetone, and benzene/toluene/xylene (BTX) requires materials with solvent stability and reliability. One of the barriers for sensors is the requirement of a semiconductor device powered by electric current. Hence, there is a need for a non-semiconductor sensing device.

SUMMARY

Embodiments of the present disclosure provide for methods of detecting, sensors (e.g., chromogenic sensor), kits, compositions, and the like that related to or use tunable macroporous polymer.

An aspect of the present disclosure provides for a method of measuring the presence of a first liquid in a liquid mixture, comprising: providing a tunable polymer membrane; and exposing an area of the tunable polymer membrane to a liquid mixture, wherein the area of the tunable polymer membrane exposed to the liquid mixture changes color if the liquid mixture includes a first liquid.

An aspect of the present disclosure provides for a chromogenic sensor, comprising: a tunable polymer membrane, wherein an area of the tunable polymer membrane has the characteristic of changing color upon exposure to a first liquid if the first liquid is present in a liquid mixture.

An aspect of the present disclosure provides for a kit for testing the presence of a first liquid, comprising: a chromogenic sensor comprising a tunable polymer membrane, wherein an area of the tunable polymer membrane has the characteristic of changing color upon exposure to a first liquid if the first liquid is present in a liquid mixture; instructions for use of the chromogenic sensor to test for the presence of the first liquid in a liquid mixture.

An aspect of the present disclosure provides for a method of making a photonic structure, comprising: disposing nanoparticles onto a surface to form a three dimensional array of particles; introducing a prepolymer mixture to the array of particles; polymerizing the prepolymer mixture to form a polymer framework around the three dimensional array of particles; and removing the particles to form a three dimensional array of macropores to form a macroporous photonic crystal membrane, wherein the three dimensional polymer framework separates the macropores.

An aspect of the present disclosure provides for a tunable polymer membrane fabricated by the method described above and herein.

Other structures, kits, methods, features, and advantages will be or become apparent to one with skill in the art upon examination of the following drawings and detailed description. It is intended that all such additional structures, kits, methods, features and advantages be included within this description, be within the scope of the present disclosure, and be protected by the accompanying claims.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles.

Moreover, in the drawings, like reference numerals designate corresponding parts throughout the several views.

(FIG. 8B) Cross-section view of a deformed area. (FIG. 8C) Cross-sectional view of a recovered area.

DETAILED DESCRIPTION

Figure 1:
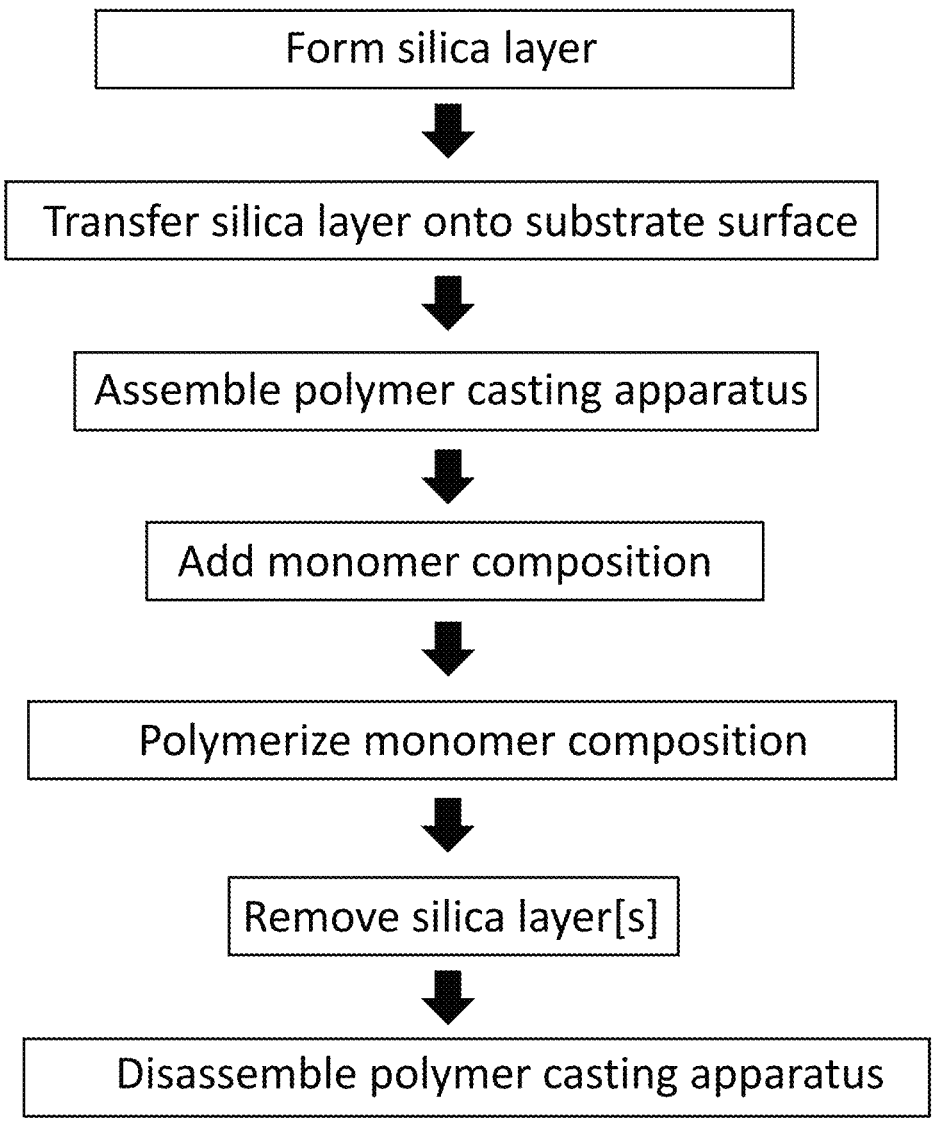
FIG. 1 illustrates an embodiment of a method for fabricating macropoorus polymer membranes using a silica nanoparticle-based photonic crystal.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, inorganic chemistry, material science, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion

Embodiments of the present disclosure provide for methods of detecting, sensors (e.g., chromogenic sensor), kits, compositions, and the like that related to or use tunable macroporous polymer. In an aspect, tunable macroporous materials as described herein can be used to determine the presence of a certain type(s) and quantity of liquid in a liquid mixture. Embodiments of the present disclosure are simple to use, provide robust results, and are re-useable while also being inexpensive.

In an aspect, the present disclosure provides for a unique macroporous structure that can be made by a simple and scalable nanoparticle self-assembly technology. This technology can result in unusual "cold" programming and subsequent room-temperature recovery, which can be cycled, for a large variety of polymers. The tunable properties are described herein. The flexibility of the methods and compositions described herein could expand and simplify the application scopes of new, tunable, materials that can be used as sensors or in methods of detecting the presence of and/or concentration of a liquid in a liquid mixture.

In an aspect, the present disclosure includes a method of measuring the presence and/or concentration of a first liquid (or multiple different types of liquids) in a liquid mixture. The liquid mixture (e.g., an aqueous or non-aqueous mixture) can optionally include a first liquid (e.g., an organic solvent). The tunable polymer membrane can be exposed to the liquid mixture in one or more ways. In an aspect, the tunable polymer membrane or a portion thereof can be dipped into the liquid mixture. In another aspect, an amount (e.g., a drop or larger amount) of the liquid mixture can be disposed onto the surface of the tunable polymer membrane. In an aspect, an area of the tunable polymer membrane can be exposed to the vapor of the liquid mixture. In an aspect, the tunable polymer membrane or a portion of thereof can be dipped into the liquid mixture.

Upon exposure of the tunable polymer membrane to the liquid mixture, the tunable polymer membrane can change color, for example from a greenish color to a bluish color, yellowish color, or orange color, depending upon the concentration of the first liquid in the liquid mixture (See Example 1). The color and color change can be tuned based on the composition of the tunable polymer membrane and/or the method of making the tunable polymer membrane. In an aspect, the color change is detectable. In one aspect, the color change is perceptible by the human eye for those that can perceive the particular colors of the color change. It is understood that some individuals have degrees of color blindness, so the color change may not be perceived by those individuals. In another aspect, the color change can be evaluated using an analysis system to measure the color change from before to after or just after the change and correlate the color change using a known standard to the identity of the first liquid and/or the concentration of the first liquid. In an aspect, the analysis system can include a mobile device such as a cell phone, tablet, or laptop, where a picture or image can be captured and subsequently be analyzed.

In an embodiment, the tunable polymer membrane can be used in a chromogenic sensor and kit to determine the presence of and/or concentration of a first fluid in the liquid mixture (e.g., the liquid form, the vapor form, or both). For example, the method, chromogenic sensor, or kit can be useful for detecting the presence or concentration of a component in fuel. In an embodiment, the first liquid can be an organic solvent that can interact with the polymer such as an alcohol (e.g., ethanol) and the liquid mixture can be an aqueous mixture or a non-aqueous mixture such as a hydrocarbon mixture like gasoline. In this regard, the method, chromogenic sensor, or kit of the present disclosure can be used to measure the amount of ethanol in the gasoline, which can be useful in situations that require low or zero ethanol in the gasoline, such as in aircraft fuel.

In regard to the kit, the kit would have instructions and optionally a wipe(s) to clean off the surface of the tunable polymer membrane, gloves, a device to expose the liquid mixture to the tunable polymer membrane, and the like. The instructions would, among other things, provide guidance on how to perform the test, evaluate the test (e.g., guide for what the color change means (e.g., presence of a first liquid, concentration of the liquid, or the like)), clean the tunable polymer membrane, use the analysis system (e.g., use the mobile device, the webpage to evaluate the results, and the like). The instructions may include other guidance as well to evaluate the contents of the liquid mixture in question.

Figure 2:
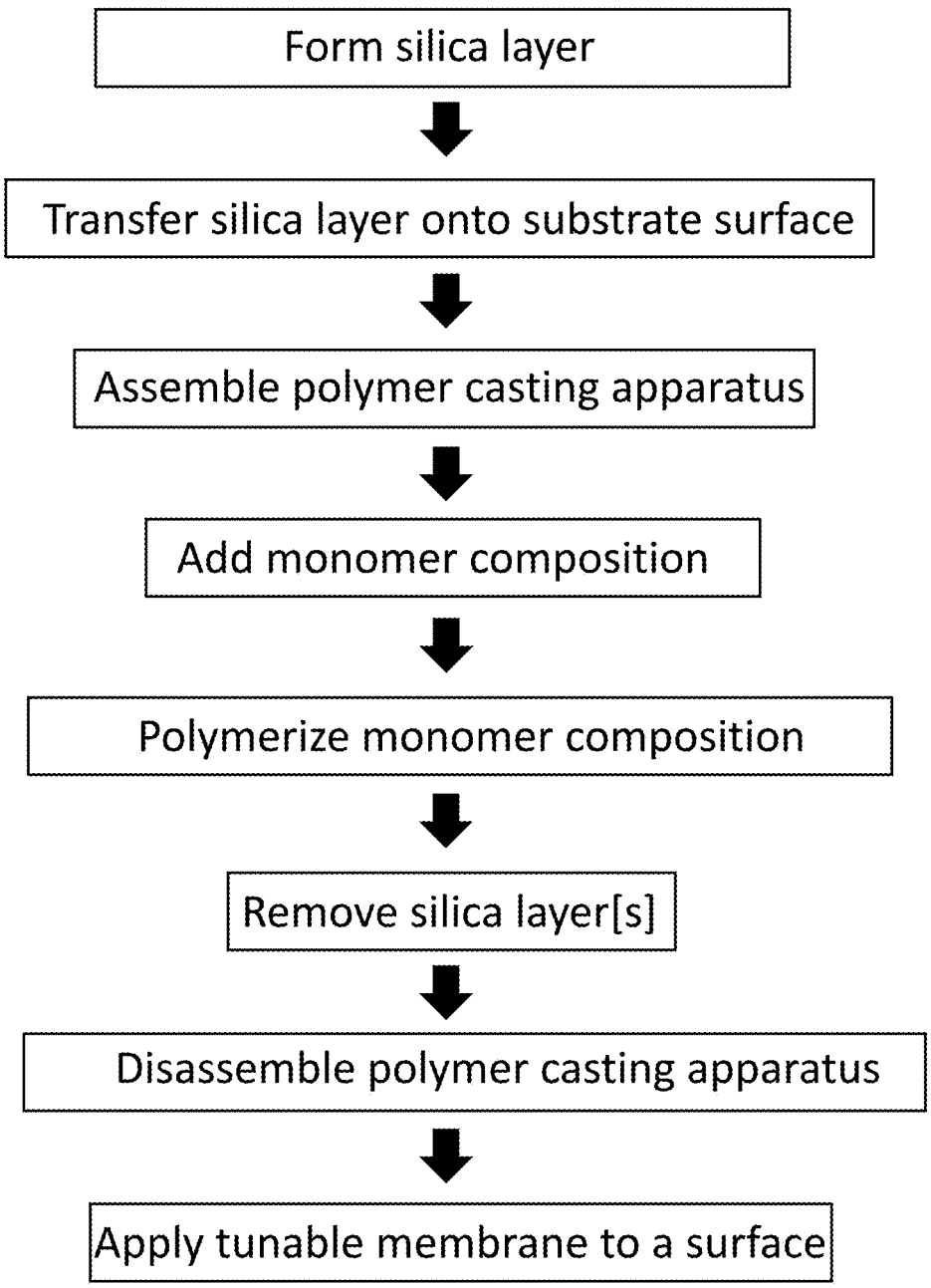
FIG. 2 illustrates a second embodiment of a method for fabricating macropoorus polymer membranes using a silica nanoparticle-based photonic crystal.
Figure 3:
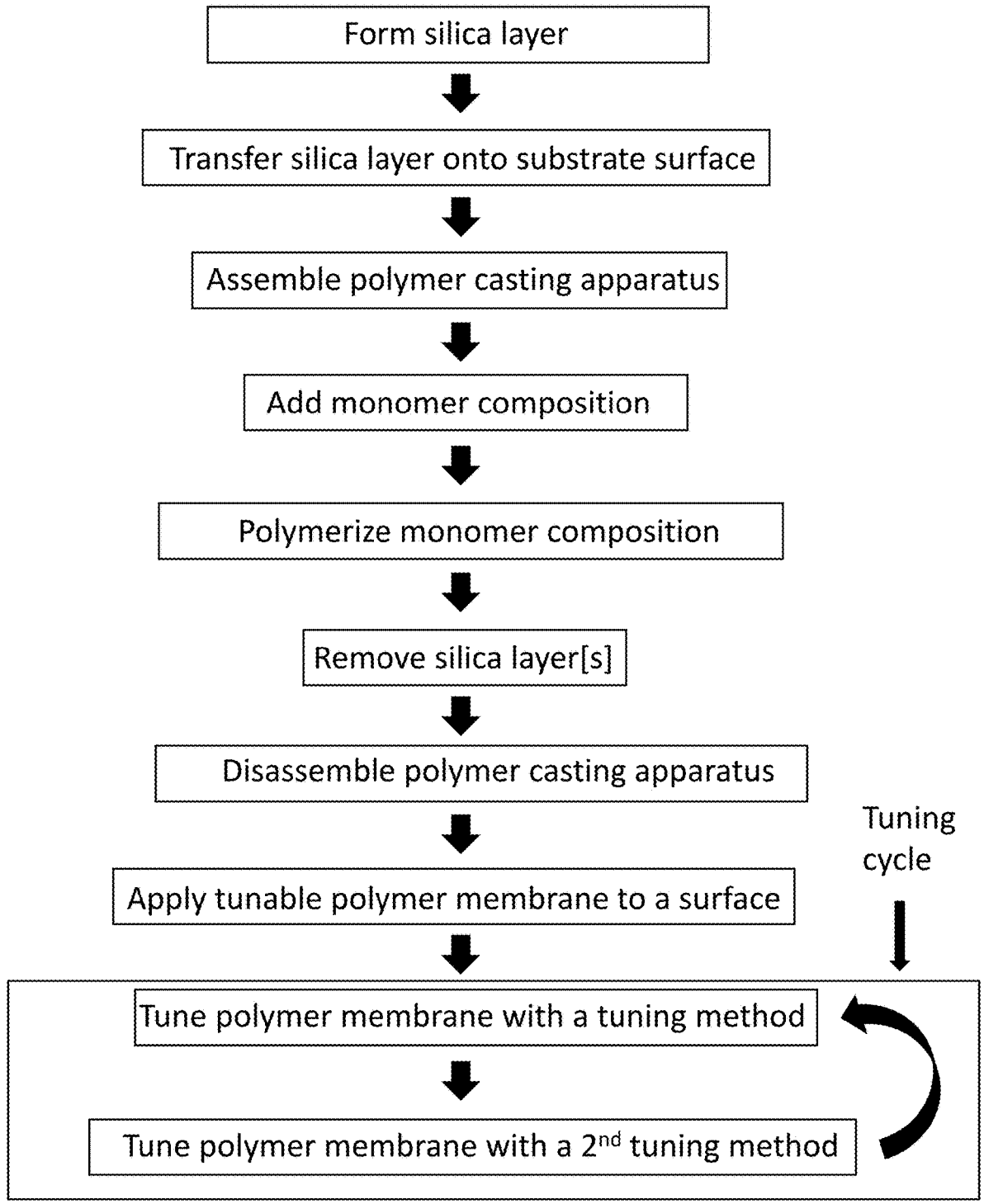
FIG. 3 illustrates a third embodiment of a method for fabricating macropoorus polymer membranes using a silica photonic crystal template.
Figure 4:
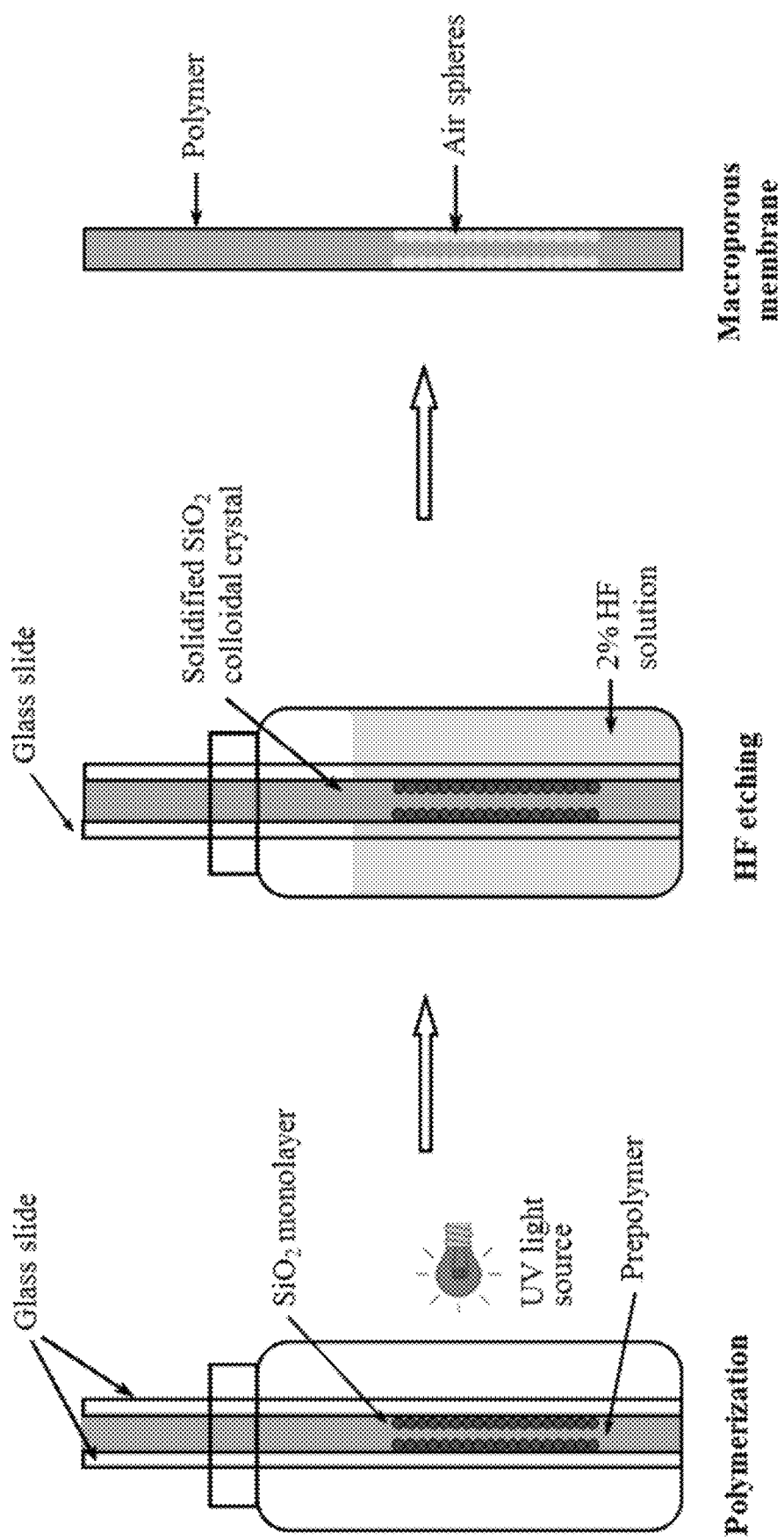
FIG. 4 illustrates a fourth embodiment of a method for fabricating macropoorus polymer membranes using a silica multilayers or single template.
Figure 5A:
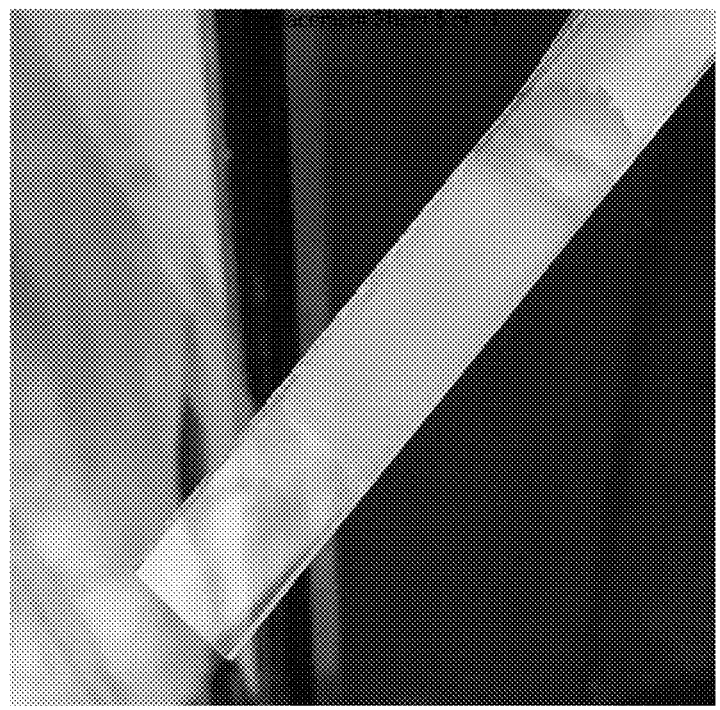
FIG. 5A is a photograph showing an example of the silica coating method described herein.
Figure 5B:
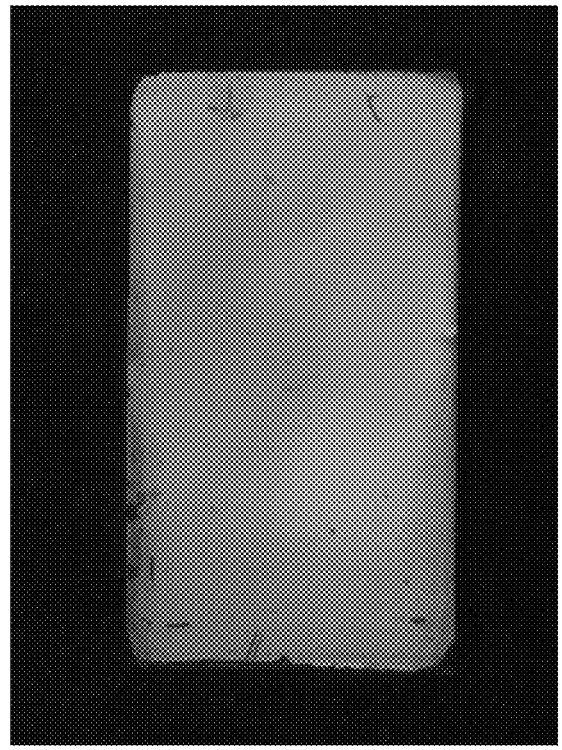
FIG. 5B depicts a photograph of a polyurethane membrane templated from FIG. 5A.

Now having described the method, sensor, and kit, additional details will be provided that describe methods for preparing tunable materials. FIGS. 1-3 are flowcharts depicting embodiments of methods described herein. FIG. 4 shows a further embodiment of a method for fabricating macroporous polymer membranes using a silica photonic crystal template In an embodiment, the colloidal crystal of silica particles can be formed by first synthesis of silica particle. Monodispersed silica particles (e.g., microspheres), with longest dimension (e.g., a diameter for a spherical particle) of about 100 to 10,000 nm, were synthesized by the standard Stöber method or other appropriate method. Silica particles were self-assembled on a substrate such as a glass microslide, which is placed in a clean scintillation vial including about 15 ml of ethanol with 1 vol % of silica particles, by the convective self-assembly technology to form colloidal crystals. Other monodispersed particles, such as polystyrene and poly(methyl methacrylate) (PMMA) particles, can also be used in assembling colloidal crystals using the convective self-assembly technology. These polymer latex particles can be selectively removed in organic solvents, such as toluene or acetone.

In an embodiment, a convective self-assembly method can enable the formation of ordered colloidal silica crystals on a glass substrate. Silica particles with a diameter of about 100 to 10,000 nm, which can be dispersed in an alcohol such as ethanol, can be assembled on the glass slides. The substrate can be varied in size depending of the desired applications.

After the silica layer or multilayer is applied, a polymer casting apparatus can be assembled. One or more substrates can be coated with a layer of silica particles as described above. In an embodiment, two or more substrates or a surface of two or more substrates can be coated with a silica layer. In an embodiment of a polymer casting apparatus, two or more coated substrates can be positioned in a container configured to hold a solvent in a sandwich-type configuration so that at least a surface of a first substrate coated with silica opposes a surface of a second substrate, uncoated or coated with silica. Other configurations can be realized with more than two coated substrates. In an embodiment, the coated substrates of the polymer casting apparatus are silica-coated glass.

In an embodiment, after assembly of the polymer casting apparatus, monomers or a monomer composition can be put in a space between two or more opposing silica coated surfaces of the two or more silica coated substrates. Monomers or a monomer composition that can form a polymer, a desired polymer, or a pre-determined polymer are described in more detail below.

After monomers are placed in the space, they can be polymerized by a polymerization method to form a tunable polymer membrane. The polymerization method can be photo-polymerization, wherein the monomers are polymerized by the application of light. In an embodiment, the light can be UV light and can be applied for a period of time.

The tunable polymer membrane can be made of a monomer, a monomer composition, or a polymer. In some embodiments, the monomers, monomer composition, or polymer can be a viscous and/or elastic polymer. The tunable polymer membrane can additionally be characterized by weak intermolecular forces. Further, the tunable polymer membrane can have a high Young's modulus and can still be reconfigurable via cold programming.

Following polymerization, the silica layers can be removed from the membrane and the membrane optionally washed. In an embodiment, the silica layer is removed by a solvent. In an embodiment, the silica is removed by 2% hydrofluoric acid (HF) aqueous solution. In an embodiment, the membrane can be washed by a wash solvent. In an embodiment, the wash solvent can be deionized water. The silica layers can be removed by a solvent that is placed in the container of the polymer casting apparatus in an embodiment. Selective removal of the silica layers can create macropores in the polymer. The polymer or tunable polymer membrane can be macroporous following removal of the templating silica layer.

In an embodiment, after removal of the silica monolayer (and optional wash), the polymer casting apparatus can be disassembled and the polymer membrane separated from the substrates that were previously silica coated. In an embodiment, the polymer membrane can be a tunable membrane.

The tunable polymer membrane can be configured to be modified such that the color of the tunable polymer membrane can vary in response to one or more liquids to which the tunable polymer membrane is exposed. The slow drying of liquid can cause a deformation of the tunable polymer membrane that changes the shape or configuration of the macropores in the tunable polymer membrane.

The color characteristics of the tunable membrane can be altered by drying after application of or cold programming. A solvent can alter the transparency by changing the shape of the macropores in the tunable polymer membrane through a mechanism such as capillary action.

The color change of the tunable polymer membrane can be cycled, or in other words is reversible. The color of the tunable polymer membrane as described herein can changed by exposure to a liquid mixture (e.g., ethanol in gasoline) and then returned to the original color by cold programming.

The methods and compositions described herein can use a large variety of shape memory polymers to form the tunable polymer membrane depending on the desired configuration of the tunable polymer membrane. Shape memory polymers (SMP) as described herein can be elastic or glassy.

A "glassy" polymer can be a polymer or copolymer with glass transition temperature higher than room temperature.

A "glassy" polymer can be optically transparent. A glassy polymer as used herein can have a glass transition state ($T_g$) higher than room temperature. In an embodiment, a glassy polymer has a $T_g$ of about 120° C. In an embodiment, the glassy polymer is poly(urethane) (with a typical $T_g$ of about 90° C.), polyethylene terephthalate (PET) and polyethyleneoxide (PEO), epoxy, polyarylates, block copolymers containing polystyrene and poly(1,4-butadiene), and poly(2-methyl-2-oxazoline) and polytetrahydrofuran, polynorbornene, and other types of shape memory polymers.

In an embodiment, a polymer or tunable polymer membrane as used herein can be polymerized poly(urethane). In an embodiment, a polymer as used herein is a glassy membrane comprising poly(urethane)s. A coating as described herein can be a glassy membrane. A coating as described herein can be a glassy membrane comprising poly(urethane)s. In an embodiment, a glassy polymer can be used to form a membrane. In an embodiment, poly(urethane)s can be used to form a membrane.

A silica nanoparticle monolayer can be used as a structural template for fabricating macroporous polymer membranes. The templating layer can be multilayers of silica nanoparticles assembled by various methodologies, such as spin coating, dip coating, doctor blade coating, and so on. In an embodiment, the silica nanoparticles can be self-assembled or not be self-assembled and/or possess long-range ordering or not possess long-range ordering. Self-assembled silica nanoparticle monolayers can be used as described herein and can be created by a variety of methods, for example a simple and scalable Langmuir-Blodgett method as described above. As used and described herein, silica nanoparticles can be used for silica nanoparticle monolayers or multilayers. Silica nanoparticles can be $Si_xO_yH_z$, synthesized by various methodologies, including the well-established Stöber method.

In an embodiment, the silica nanoparticles can be about 100 nm to about 10,000 nm. In an embodiment, silica nanoparticles are silicon dioxide ($SiO_2$). In an embodiment, a composition of silica nanoparticles has an average diameter of about 350 nm/particle. Silica nanoparticles as used herein can have a diameter of about 350 nm. In an embodiment, silica nanoparticles as used herein can be $SiO_2$ nanoparticles with a diameter of about 350 nm each.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

In this disclosure, a templating fabricated macroporous polymer photonic crystal that responds to selected compounds can be used as a chemical sensor with fast response and high sensitivity. The system is specifically designed to detect the presence and even measuring the target chemical in a multicomponent solution (ethanol in gasoline). The detection could be done by dipping the sensor in the liquid mixture as well as placing the sensor above the solution surface, which depends on the detection limit. The selective-interaction of a target compounds with the sensor provides a unique capability for chemical detection.

Silica particles were self-assembled on a glass microslide by the convective self-assembly technology to form colloidal crystals. Various thickness of resulting colloidal crystals (10-50 layers) were observed as a result of different particle volume fraction of the silica microspheres/ethanol suspension. The microslide with silica colloidal crystal was then allowed to stick to a blank microslide with a ~1 mm thick spacer in between. Next, a viscous oligomer mixture (CN945A70, Sartomer) consisting of trifunctional acrylated urethane, tripropylene glycol diacrylate (TPGDA), and photoinitiator (Darocur 1173, 2-hydroxy-2-methyl-1-phenyl-1-propanone, BASF) was preheated to 90° C. and then transferred into the space between the microslides. The capillary force assisted the infiltration of the oligomer mixture into the interstitial of silica microspheres and was evident as the oligomer mixture and silica particle index-matched and the sample cell turned transparent. The sample was then polymerized using a pulsed UV curing system (RC 742, Xenon) for 4 s. Last, the polymerized sample was removed from the glass microslide and subsequently soaked in a 1 vol % hydrofluoric acid aqueous solution for 24 h. The etched sample was rinsed with deionized water, ethanol and dried in air. The final product is in greenish diffractive color when observed at large viewing angles (>45°).

Figure 6:
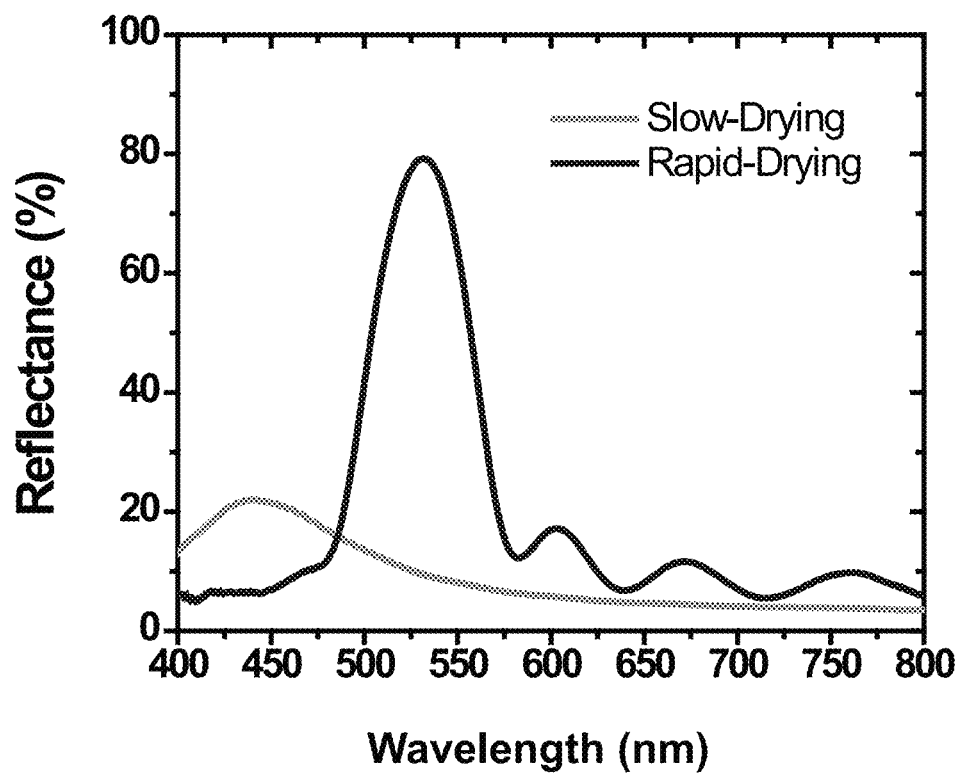
FIG. 6 illustrates normal-incidence transmission spectra obtained from the macroporous polymer film with different drying rates.

Cold programming experiments on the free-standing macroporous polymer film were performed where organic solvent (e.g., acetone and acetonitrile) was added dropwise on the film surface. Greenish diffractive color remained when the solvent was removed within 5 seconds using Kimwipes™ or air dry (FIG. 6. blue-peak). The original diffractive colors were changed/lost after we leave the solvent on the surface and dried naturally in ~2 min (FIG. 6 orange-peak).

Figure 7:
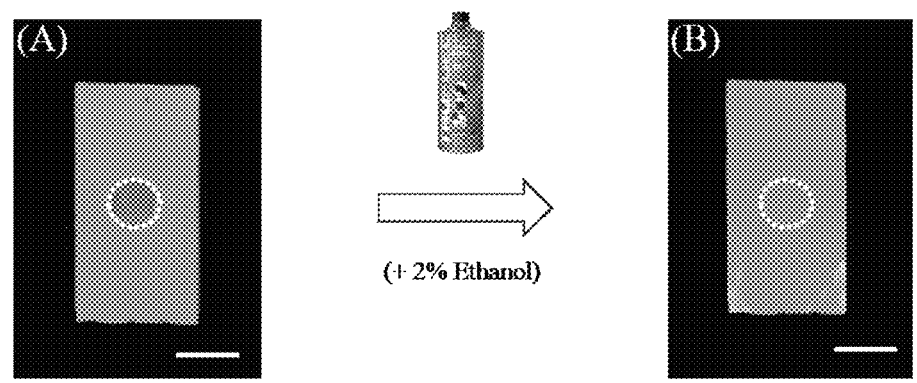
FIG. 7 illustrates a photograph of a macroporous polymer film dipping in a commercial ethanol-free fuel (TruFuel®) blended with 2% of ethanol. Polymer film with deformation at the center before (A) and after (B). Scale bar: 5 mm.
Figure 8A:
FIGS. 8A-C illustrate typical SEM images of (FIG. 8A) Cross-section view of a greenish area from a macroporous polymer film.
Figure 8B:
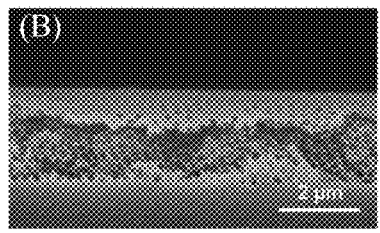
Figure 8C:

The bluish-iridescent color of the deformed areas is caused by the Bragg diffraction of visible light from the deformed macroporous film (see FIG. 7B). FIG. 8A shows the top-view SEM image of the greenish original area from the macroporous polymer film. FIG. 8B is the cross-sectional SEM image of a bluish deformed area of the macroporous polymer film. The recovered of the macroporous 3-D order is shown by the cross-sectional SEM image in FIG. 8C.

Figure 9:
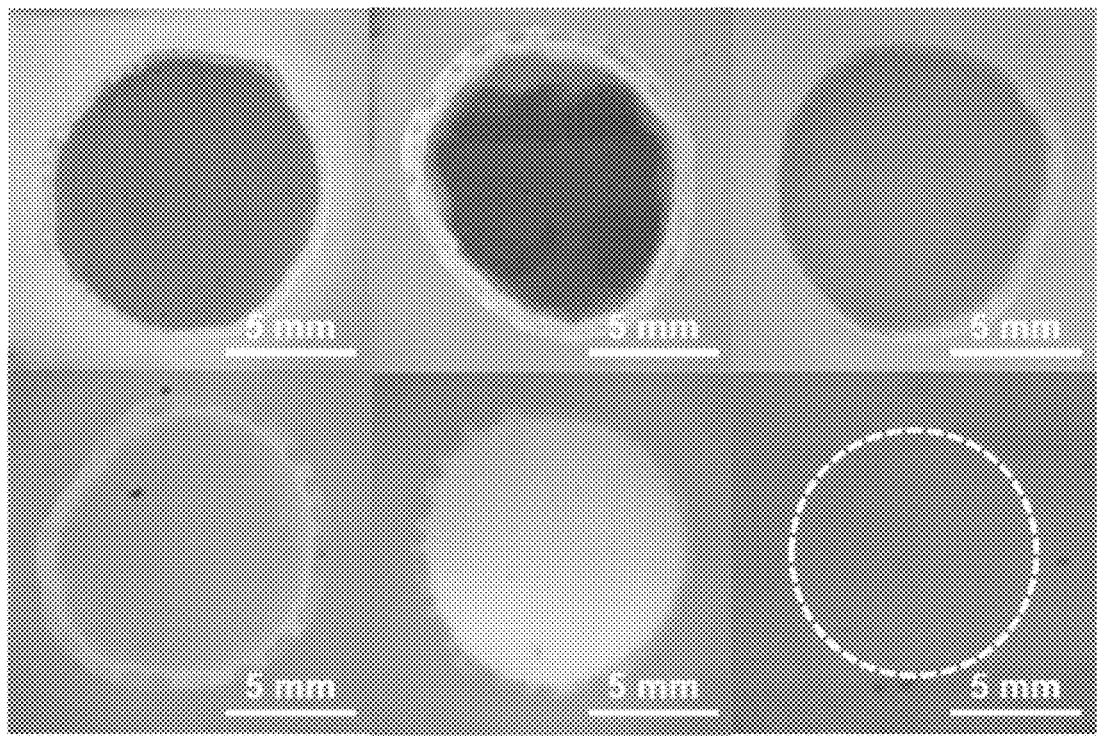
FIG. 9 illustrates an image of chromogenic sensor for ethanol sensing.

We utilized this unique cold programming cycle (deform and then recovery) with all-room-temperature-approach to design a chromogenic sensor, which uses the degree of recovery as a sensing parameter. A chromogenic sensor was fabricated to demonstrate the visible color change when in contact with different concentration of the analyte, which is ethanol in this case. In FIG. 9, the sample changed from transparent to blue, yellow, then orange, when exposed to different concentrations of ethanol in gasoline (0 ppm, 2000 ppm, 3000 ppm, 4000 ppm, 5000 ppm, 6000 ppm, respectively). Furthermore, the response time of the chromogenic sensor was less than ~3 seconds.

Figure 10:
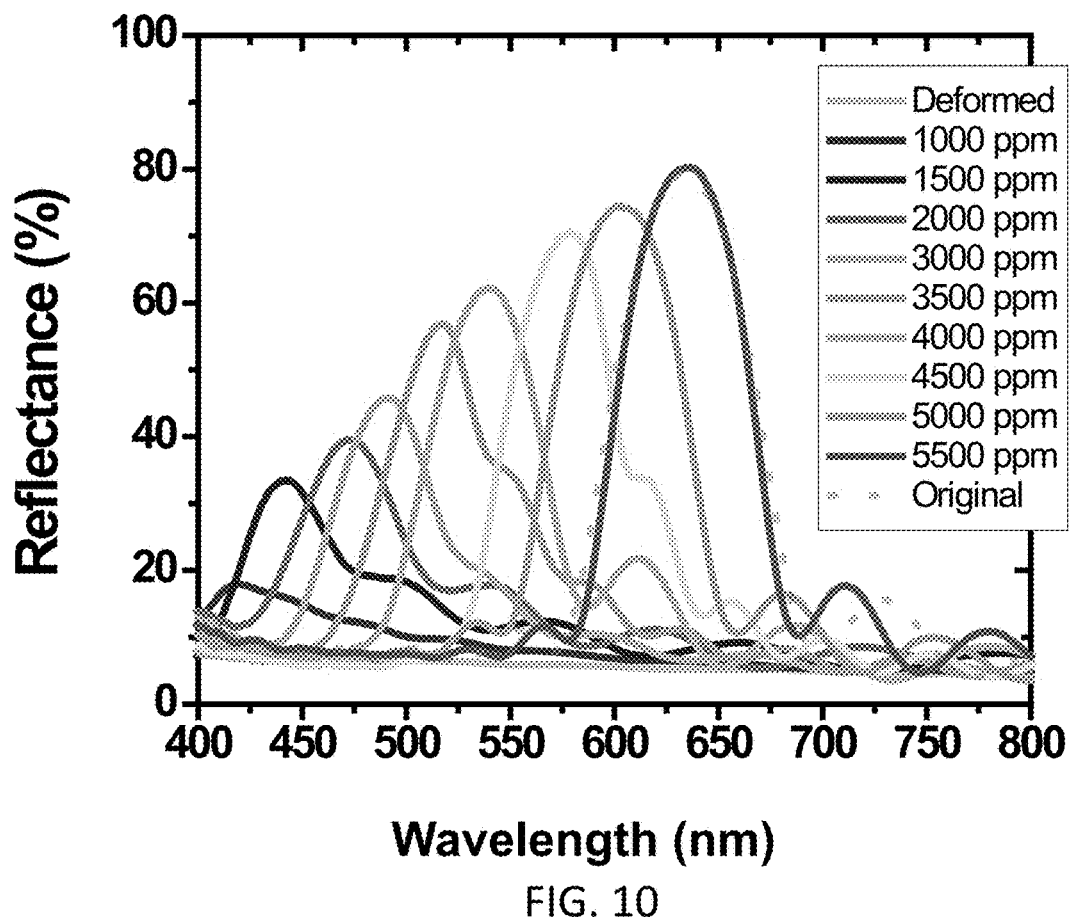
FIG. 10 illustrates specular optical reflection spectra for detecting different concentrations of ethanol blended with octane.

The ethanol in gasoline (mostly alkanes) swells the SMP chromogenic sensor, and the degree of swelling is higher when the concentration of ethanol is greater. To further study the precise effect of swelling and ethanol concentration, we utilized a two-component system—ethanol in octane. By using a vis-NIR spectrometer, we could obtain a concentration dependence spectra due to the light diffraction of SMP with a response time of 5 s. The SMP begins at fully deformed state, and then gradually recovers with increasing ethanol concentration. The SMP is fully recovered when the ethanol concentration is at 5500 ppm (FIG. 10).

Figure 11:
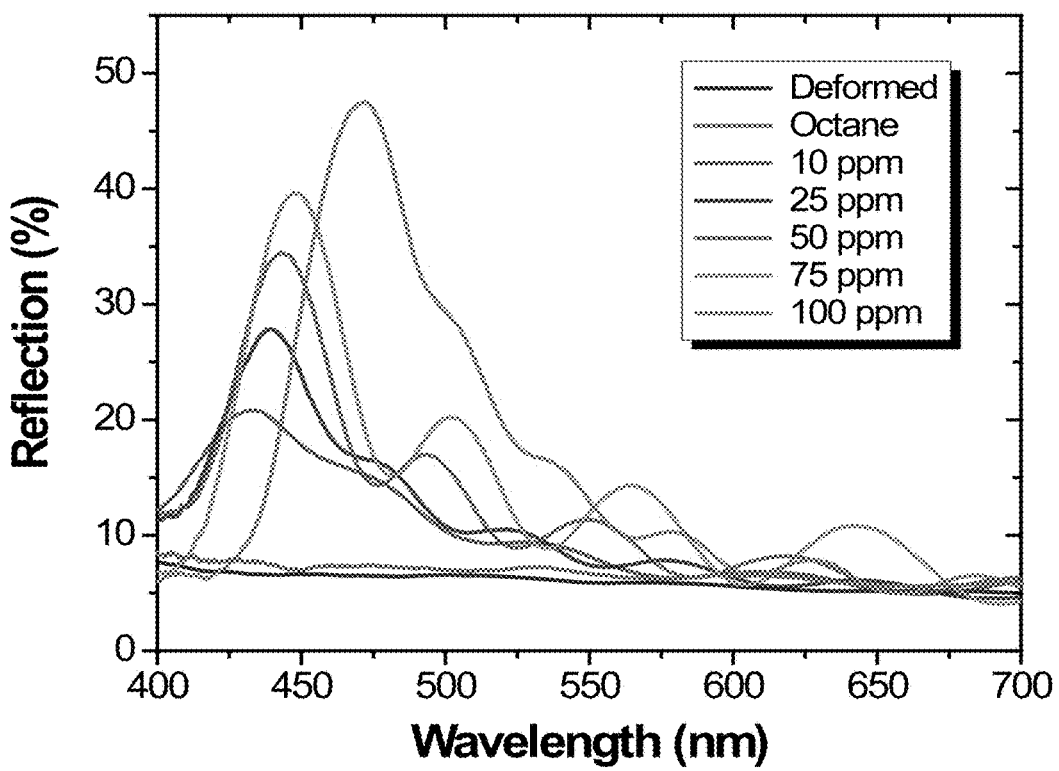
FIG. 11 illustrates specular optical reflection spectra for detecting trace amount of ethanol blended with octane.

To further explore the sensitivity at low concentration, we experiment the SMP by allowing the sensor to response for 8 h under extremely low ethanol concentrations (FIG. 11). The optical spectra show a distinct diffraction response for ethanol concentration as low as 10 ppm, magenta curve.

Figure 12:
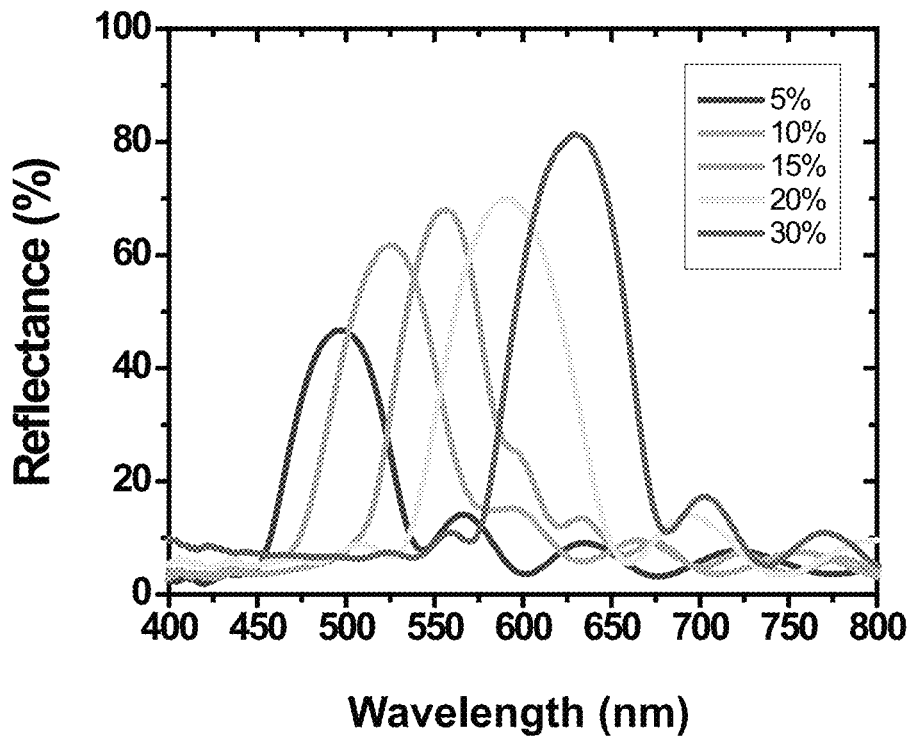
FIG. 12 illustrates specular optical reflection spectra for detecting ethanol vapor above ethanol-octane mixtures with different ethanol concentrations.
Figure 13:
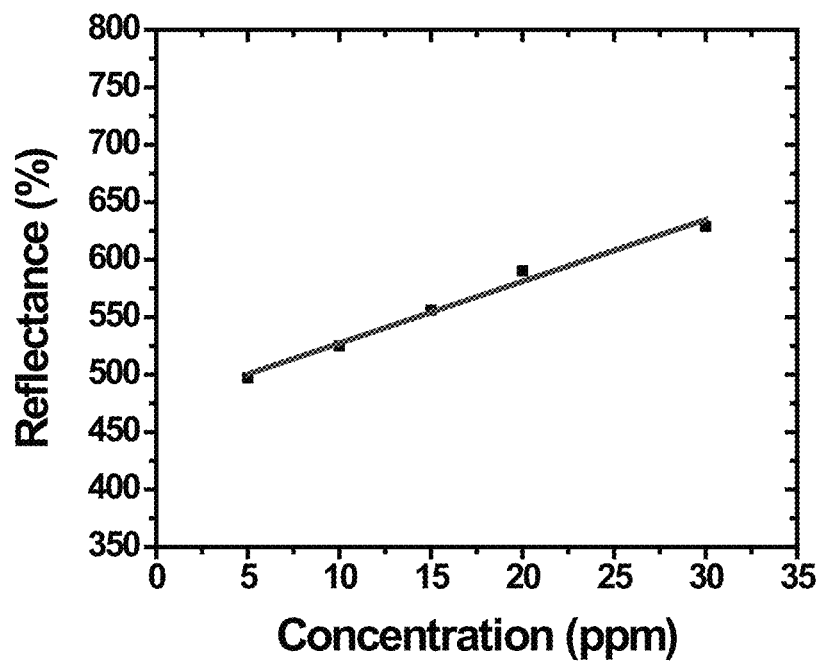
FIG. 13 illustrates a linear relationship between the positions of the optical reflection peaks and the ethanol concentrations in ethanol-octane mixtures.

Low concentration aside, our chromogenic sensor could also detect ethanol at relatively high concentration. The idea is to distinguish ethanol concentration in gasoline by using its relative vapor pressure. FIG. 12 shows the reflection spectra of the SMP when sensing the vapor of various gasoline with ethanol content ranging from 5-30 vol %. The SMP had a gradual red shift as the concentration of ethanol, hence the vapor pressure of ethanol, increased from 5% to 30%. FIG. 13 illustrates an optical characterization of ethanol sensor with ethanol vapor when the concentration increases from 5 to 30 vol %.

Figure 14A:
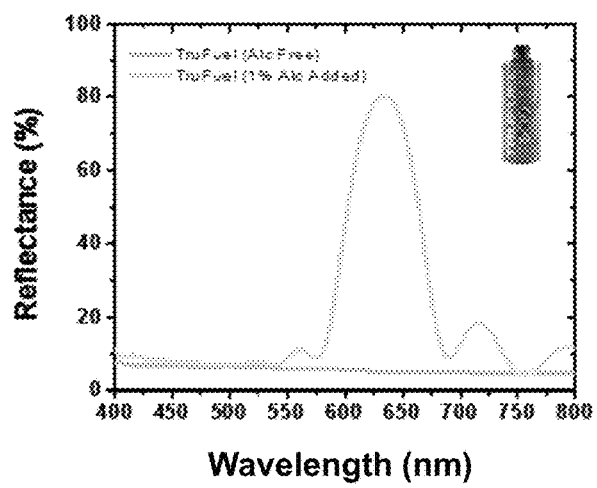
FIGS. 14A-D illustrate specular optical reflection spectra for detecting ethanol in ethanol-free TruFuel®, Shell® gasoline, NyQuil™ medicine, and mouthwash liquids.
Figure 14B:
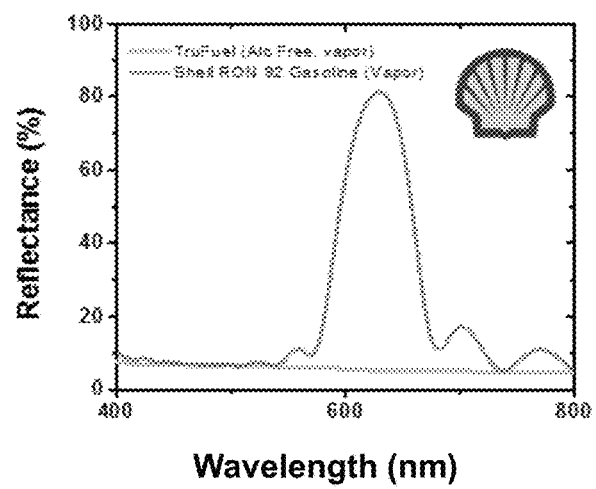
Figure 14C:
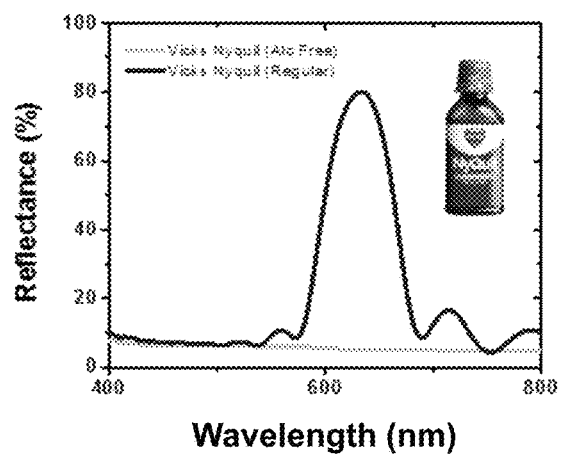
Figure 14D:
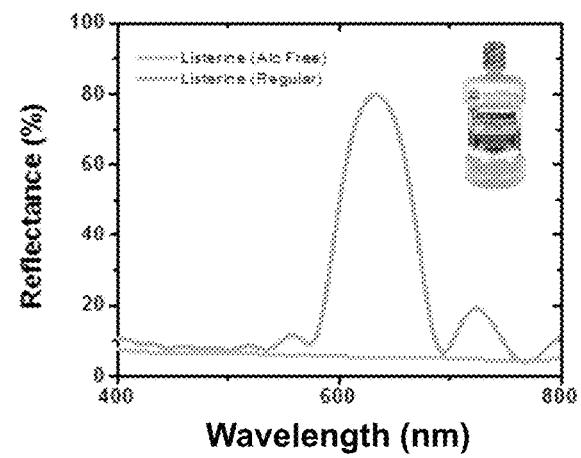

Moreover, sensing experiments were performed using commercial products. The deformed polymer was used to test commercial product with ethanol and its control product that is ethanol-free. First, we investigate our sensor performance for gasoline. We first test the sensor with TruFuel®, which is a commercially sold ethanol free gasoline with 92 octane number. The optical spectra show both flat curve in grey color (FIGS. 14A-D). Then, the sensors were separately deformed and triggered by using TruFuel® with 1% of ethanol added and Shell® gasoline in liquid and vapor respectively. Both shows orange iridescent peak ~630 nm (yellow and orange peak in FIGS. 14A and 14B, respectively). We then carried out a test for various pharmaceutical products. The chromogenic sensor shows no color change when triggered by ethanol free Nyquil™. Whereas the sample triggered with regular Nyquil™ shows significant color change (dark blue peak in FIG. 14C). The same result is presented when the sensor use to distinguish daily supplies such as mouthwash. The sensor could differentiate commercially sold ethanol free Listerine to regular ones (FIG. 14D).

Figure 15:
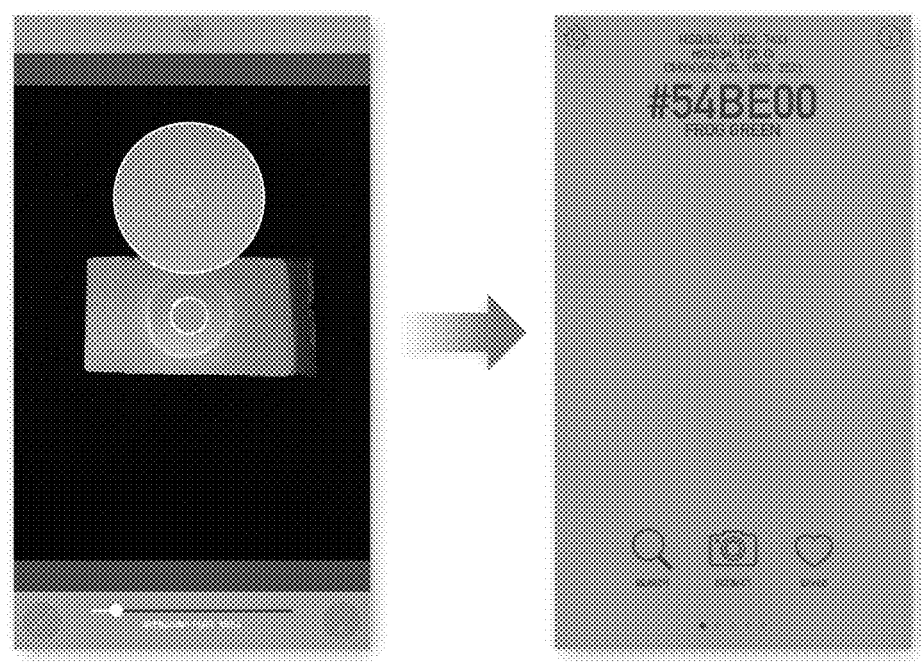
FIG. 15 illustrates schematics of smartphone-based sensor analysis procedure.
Figure 16:
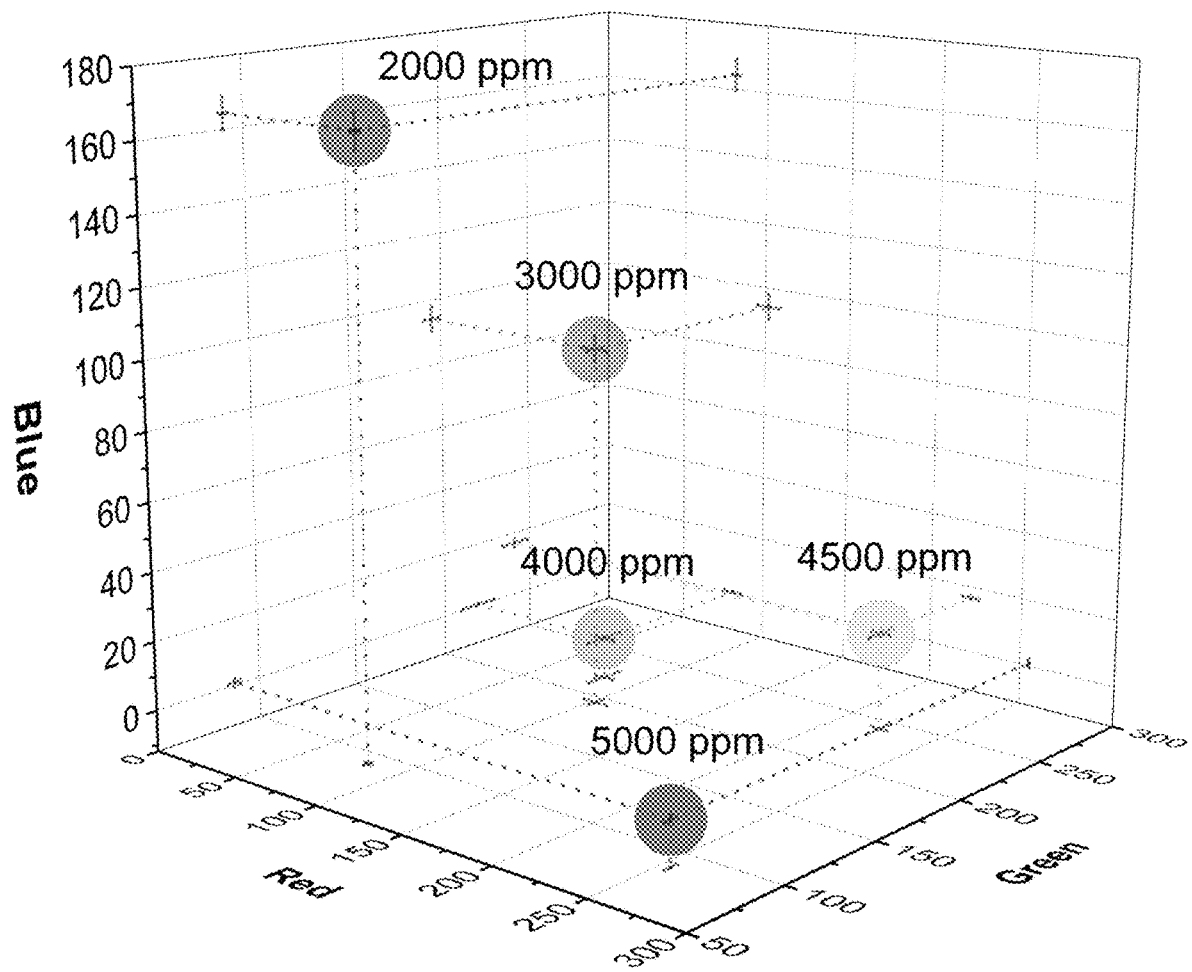
FIG. 16 illustrates a database of smartphone analysis to compare RGB data to ethanol concentration.

Lastly, we developed a chromogenic sensor analysis tool using smartphones (FIG. 15). We generated an RGB calorimetric profile database of the SMP sensor when exposed to ethanol with known concentration (FIG. 16). When a customer captured a new image for analysis, its RGB data will show in the app, and the results could be looked up in the database for analysis. We believe our unique SMP-based sensor and instant analysis system can be easily extended to the analysis of many more target chemicals in the desired system.

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, %, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about 'y'".

Unless defined otherwise, all technical and scientific terms used have the same meaning as commonly understood by one of ordinary skill in the art to which this disclosure belongs. Although any methods and materials similar or equivalent to those described can also be used in the practice or testing of the present disclosure, the preferred methods and materials are now described.

Embodiments of the present disclosure will employ, unless otherwise indicated, techniques of separating, testing, and constructing materials, which are within the skill of the art. Such techniques are explained fully in the literature.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

We claim:

1. A chromogenic sensor, comprising:
   a tunable shape memory polymer membrane,
      wherein the tunable shape memory polymer membrane is an optically transparent glassy polymer having a glass transition temperature higher than room temperature,
      wherein the glassy polymer is selected from poly (urethane), polyethylene terephthalate (PET), polyethyleneoxide (PEO), epoxy, polyarylates, block copolymers containing polystyrene and poly(1,4-butadiene), poly(2-methyl-2-oxazoline), and polytetrahydrofuran, and polynorbornene,
      wherein the tunable shape memory polymer membrane is a macroporous photonic crystal membrane having a three-dimensional polymer framework separating macropores; and
   wherein when an area of the tunable shape memory polymer membrane is exposed to a liquid mixture containing a first liquid, the area changes color if the liquid mixture includes the first liquid;
   wherein the color change is correlated to a concentration of the first liquid in the liquid mixture or is correlated to a pressure of vapor of the first liquid in the liquid mixture;
   wherein the area changes color depending upon the concentration of the first liquid in the liquid mixture,
      wherein the color changes from a greenish color to a bluish color in response to a first concentration, yellowish color in response to a second concentration, and orange color in response to a third concentration, and
      wherein the first concentration, the second concentration, and the third concentration are different from one another.

2. The chromogenic sensor of claim 1, wherein the liquid mixture is an aqueous mixture or a non-aqueous mixture.

3. The chromogenic sensor of claim 1, wherein the first liquid is an organic solvent.

4. The chromogenic sensor of claim 3, wherein the organic solvent is ethanol.

5. The chromogenic sensor of claim 1, wherein the liquid mixture is gasoline.

* * * * *